United States Patent
You et al.

(10) Patent No.: US 11,999,065 B2
(45) Date of Patent: Jun. 4, 2024

(54) ROBOTIC SURGICAL SYSTEM WITH MOTORIZED MOVEMENT TO A STARTING POSE FOR A REGISTRATION OR CALIBRATION ROUTINE

(71) Applicant: MAKO Surgical Corp., Weston, FL (US)

(72) Inventors: Zhifu You, Palmetto Bay, FL (US); Steve Polomski, Kinnelon, NJ (US); Curtis McClarin, Fort Lauderdale, FL (US); Jason Otto, Sioux Falls, SD (US); Abdullah Abbasi, San Diego, CA (US)

(73) Assignee: MAKO Surgical Corp., Weston, FL (US)

( * ) Notice: Subject to any disclaimer, the term of this patent is extended or adjusted under 35 U.S.C. 154(b) by 400 days.

(21) Appl. No.: 17/513,324

(22) Filed: Oct. 28, 2021

(65) Prior Publication Data
US 2022/0134569 A1    May 5, 2022

Related U.S. Application Data

(60) Provisional application No. 63/189,508, filed on May 17, 2021, provisional application No. 63/131,654, (Continued)

(51) Int. Cl.
*B25J 9/16* (2006.01)
*A61B 17/14* (2006.01)
(Continued)

(52) U.S. Cl.
CPC .......... *B25J 9/1664* (2013.01); *A61B 17/142* (2016.11); *A61B 34/20* (2016.02); *A61B 34/25* (2016.02);
(Continued)

(58) Field of Classification Search
CPC ...... B25J 9/1664; B25J 9/1689; B25J 9/1692; A61B 17/142; A61B 34/20; A61B 34/25;
(Continued)

(56) References Cited

U.S. PATENT DOCUMENTS 4,559,936 A    12/1985  Hill
5,078,140 A     1/1992  Kwoh
(Continued)

FOREIGN PATENT DOCUMENTS

EP    1 518 501 A2    3/2005
EP    1 690 503 A1    8/2006
(Continued)

OTHER PUBLICATIONS

US 9,445,923, 9/2016, Arthromeda, Inc. (withdrawn)
(Continued)

*Primary Examiner* — Abby Y Lin
*Assistant Examiner* — Dylan M Katz
(74) *Attorney, Agent, or Firm* — FOLEY & LARDNER LLP

(57) ABSTRACT

A surgical system includes a robotic arm extending from a base, a tracking system configured to track at least one of a first marker attached to a distal end of the robotic arm and a second marker attached to the base, and a controller. The controller is configured to obtain an indication that the base is in position for performing a surgical operation, determine a starting pose for a registration routine for the robotic arm, control the robotic arm to automatically move to the starting pose for the registration or calibration routine, and in response to successful automatic movement to the starting pose for the registration or calibration routine, perform the registration or calibration routine for the robotic arm.

20 Claims, 8 Drawing Sheets

Related U.S. Application Data filed on Dec. 29, 2020, provisional application No. 63/125,481, filed on Dec. 15, 2020, provisional application No. 63/107,781, filed on Oct. 30, 2020.

(51) Int. Cl.
- *A61B 34/00* (2016.01)
- *A61B 34/20* (2016.01)
- *A61B 34/30* (2016.01)
- *A61B 34/32* (2016.01)
- *G05B 15/02* (2006.01)
- *G16H 20/40* (2018.01)
- *G16H 40/67* (2018.01)

(52) U.S. Cl.
CPC .............. *A61B 34/30* (2016.02); *A61B 34/32* (2016.02); *B25J 9/1689* (2013.01); *B25J 9/1692* (2013.01); *G05B 15/02* (2013.01); *G16H 20/40* (2018.01); *G16H 40/67* (2018.01); *A61B 2034/2055* (2016.02); *A61B 2034/2059* (2016.02); *A61B 2034/252* (2016.02)

(58) Field of Classification Search
CPC . A61B 34/30; A61B 34/32; A61B 2034/2055; A61B 2034/2059; A61B 2034/252; A61B 2034/107; A61B 2034/108; A61B 2034/2068; G05B 15/02; G16H 20/40; G16H 40/67
See application file for complete search history.

(56) References Cited

U.S. PATENT DOCUMENTS

| | | |
|---|---|---|
| 5,413,573 A | 5/1995 | Koivukangas |
| 5,540,696 A | 7/1996 | Booth et al. |
| 5,630,431 A | 5/1997 | Taylor |
| 5,682,886 A | 11/1997 | Delp et al. |
| 5,800,438 A | 9/1998 | Tuke et al. |
| 5,824,085 A | 10/1998 | Sahay et al. |
| 6,328,752 B1 | 12/2001 | Sjostrom et al. |
| 6,595,997 B2 | 7/2003 | Axelson et al. |
| 6,685,711 B2 | 2/2004 | Axelson et al. |
| 6,758,850 B2 | 7/2004 | Smith et al. |
| 6,827,723 B2 | 12/2004 | Carson |
| 6,859,661 B2 | 2/2005 | Tuke |
| 7,008,362 B2 | 3/2006 | Fitzgibbon |
| 7,412,897 B2 | 8/2008 | Crottet et al. |
| 7,510,557 B1 | 3/2009 | Bonutti |
| 7,547,307 B2 | 6/2009 | Carson et al. |
| 7,591,821 B2 | 9/2009 | Kelman |
| 7,607,440 B2 | 10/2009 | Coste-Maniere et al. |
| 7,618,421 B2 | 11/2009 | Axelson et al. |
| 7,634,306 B2 | 12/2009 | Sarin et al. |
| 7,670,345 B2 | 3/2010 | Plassky et al. |
| 7,696,899 B2 | 4/2010 | Immerz et al. |
| 7,794,467 B2 | 9/2010 | Mcginley et al. |
| 7,809,421 B1 * | 10/2010 | Govari ................. A61B 5/062 600/407 |
| 7,831,295 B2 | 11/2010 | Friedrich et al. |
| 7,927,336 B2 | 4/2011 | Rasmussen |
| 7,931,655 B2 | 4/2011 | Axelson et al. |
| 7,945,310 B2 | 5/2011 | Gattani et al. |
| 7,963,913 B2 | 6/2011 | Devengenzo et al. |
| 8,007,448 B2 | 8/2011 | Moctezuma De La Barrera |
| 8,010,180 B2 | 8/2011 | Quaid et al. |
| 8,038,683 B2 | 10/2011 | Couture et al. |
| 8,075,317 B2 | 12/2011 | Youngblood |
| 8,078,440 B2 | 12/2011 | Otto et al. |
| 8,096,997 B2 | 1/2012 | Plaskos et al. |
| 8,109,942 B2 | 2/2012 | Carson |
| 8,116,847 B2 | 2/2012 | Gattani et al. |
| 8,126,533 B2 | 2/2012 | Lavallee |
| 8,160,345 B2 | 4/2012 | Pavlovskaia et al. |
| 8,170,888 B2 | 5/2012 | Silverman |
| 8,172,775 B2 | 5/2012 | Warkentine et al. |
| 8,197,549 B2 | 6/2012 | Amirouche et al. |
| 8,257,360 B2 | 9/2012 | Richard et al. |
| 8,265,790 B2 | 9/2012 | Amiot et al. |
| 8,265,949 B2 | 9/2012 | Haddad |
| 8,277,455 B2 | 10/2012 | Couture et al. |
| 8,337,508 B2 | 12/2012 | Lavallee et al. |
| 8,357,111 B2 | 1/2013 | Caillouette et al. |
| 8,377,129 B2 | 2/2013 | Fitz et al. |
| 8,382,765 B2 | 2/2013 | Axelson et al. |
| 8,386,077 B2 | 2/2013 | Birkenbach et al. |
| 8,480,679 B2 | 7/2013 | Park et al. |
| 8,483,469 B2 | 7/2013 | Pavlovskaia et al. |
| 8,521,252 B2 | 8/2013 | Diez |
| 8,545,509 B2 | 10/2013 | Park et al. |
| 8,548,559 B2 | 10/2013 | Hodgson et al. |
| 8,551,023 B2 | 10/2013 | Sherman et al. |
| 8,551,099 B2 | 10/2013 | Lang et al. |
| 8,626,267 B2 | 1/2014 | Lavallee |
| 8,641,726 B2 | 2/2014 | Bonutti |
| 8,682,052 B2 | 3/2014 | Fitz et al. |
| 8,707,963 B2 | 4/2014 | Davis et al. |
| 8,715,291 B2 | 5/2014 | Park et al. |
| 8,721,568 B2 | 5/2014 | Rock et al. |
| 8,777,875 B2 | 7/2014 | Park |
| 8,801,719 B2 | 8/2014 | Park et al. |
| 8,801,720 B2 | 8/2014 | Park et al. |
| 8,832,019 B2 | 9/2014 | Gao |
| 8,834,490 B2 | 9/2014 | Bonutti |
| 8,845,645 B2 | 9/2014 | Wilkinson et al. |
| 8,861,818 B2 | 10/2014 | Ito et al. |
| 8,880,152 B2 | 11/2014 | Lavallee |
| 8,885,904 B2 | 11/2014 | Darrow et al. |
| 8,938,282 B2 | 1/2015 | Daon et al. |
| 8,951,260 B2 | 2/2015 | Lang et al. |
| 8,956,355 B2 | 2/2015 | Edwards et al. |
| 8,965,483 B2 | 2/2015 | Couture et al. |
| 8,974,468 B2 | 3/2015 | Borja |
| 8,979,859 B2 | 3/2015 | Leparmentier et al. |
| 9,002,426 B2 | 4/2015 | Quaid et al. |
| 9,101,394 B2 | 8/2015 | Arata et al. |
| 9,119,722 B1 | 9/2015 | Kusuma |
| 9,125,669 B2 | 9/2015 | Ranawat et al. |
| 9,167,989 B2 | 10/2015 | Odermatt et al. |
| 9,168,153 B2 | 10/2015 | Bettenga |
| 9,173,716 B2 | 11/2015 | Kasodekar et al. |
| 9,186,292 B2 | 11/2015 | Besendorfer |
| 9,220,510 B2 | 12/2015 | Cheal et al. |
| 9,237,951 B1 | 1/2016 | Hakki |
| 9,241,801 B1 | 1/2016 | Parry et al. |
| 9,247,998 B2 | 2/2016 | Hladio et al. |
| 9,248,001 B2 | 2/2016 | Colombet et al. |
| 9,259,290 B2 | 2/2016 | Jenkins et al. |
| 9,262,802 B2 | 2/2016 | Aghazadeh |
| 9,265,447 B2 | 2/2016 | Stein et al. |
| 9,271,756 B2 | 3/2016 | Van Der Walt et al. |
| 9,277,968 B2 | 3/2016 | Min et al. |
| 9,286,355 B2 | 3/2016 | De Guise et al. |
| 9,289,264 B2 | 3/2016 | Iorgulescu et al. |
| 9,301,812 B2 | 4/2016 | Kehres et al. |
| 9,332,987 B2 | 5/2016 | Leimbach et al. |
| 9,406,134 B2 | 8/2016 | Klingenbeck-Regn |
| 9,433,425 B2 | 9/2016 | Wilkinson |
| 9,439,656 B2 | 9/2016 | Chana et al. |
| 9,517,000 B2 | 12/2016 | Donhowe et al. |
| 9,532,788 B2 | 1/2017 | Jordan et al. |
| 9,532,838 B2 | 1/2017 | Coste-Maniere et al. |
| 9,549,742 B2 | 1/2017 | Berend et al. |
| 9,549,782 B2 | 1/2017 | Park et al. |
| 9,554,953 B2 | 1/2017 | Dirauf et al. |
| 9,561,082 B2 | 2/2017 | Yen et al. |
| 9,572,682 B2 | 2/2017 | Aghazadeh |
| 9,585,725 B2 | 3/2017 | Bonutti |
| 9,585,768 B2 | 3/2017 | Sherman et al. |
| 9,592,133 B2 | 3/2017 | Toler et al. |
| 9,597,096 B2 | 3/2017 | Aghazadeh |
| 9,610,086 B2 | 4/2017 | Park et al. |

(56) References Cited

U.S. PATENT DOCUMENTS

| | | |
|---|---|---|
| 9,610,134 B2 | 4/2017 | Kubiak et al. |
| 9,639,156 B2 | 5/2017 | Iorgulescu et al. |
| 9,684,768 B2 | 6/2017 | Lavallee et al. |
| 9,700,292 B2 | 7/2017 | Nawana et al. |
| 9,724,165 B2 | 8/2017 | Arata et al. |
| 9,737,311 B2 | 8/2017 | Lavallee et al. |
| 9,737,369 B2 | 8/2017 | Burger et al. |
| 9,763,683 B2 | 9/2017 | Bonutti |
| 9,763,746 B2 | 9/2017 | Deichmann et al. |
| 9,782,226 B2 | 10/2017 | Park et al. |
| 9,782,229 B2 | 10/2017 | Crawford et al. |
| 9,808,356 B2 | 11/2017 | Haight et al. |
| 9,848,896 B2 | 12/2017 | Emslie et al. |
| 9,861,446 B2 | 1/2018 | Lang |
| 9,888,931 B2 | 2/2018 | Bake |
| 9,901,404 B2 | 2/2018 | Park et al. |
| 9,901,463 B2 | 2/2018 | Mahfouz |
| 9,911,187 B2 | 3/2018 | Steinle et al. |
| 9,913,691 B2 | 3/2018 | Brooks |
| 9,913,692 B2 | 3/2018 | Arata et al. |
| 9,916,421 B2 | 3/2018 | Vorhis et al. |
| 9,987,092 B2 | 6/2018 | Hladio et al. |
| 10,010,377 B2 | 7/2018 | Iorgulescu et al. |
| 10,052,164 B2 | 8/2018 | Overmyer |
| 10,070,931 B2 | 9/2018 | Itkowitz et al. |
| 10,070,973 B2 | 9/2018 | Sherman et al. |
| 10,071,488 B2 | 9/2018 | Robinson et al. |
| 10,076,344 B2 | 9/2018 | Toler |
| 10,080,616 B2 | 9/2018 | Wilkinson et al. |
| 10,092,361 B2 | 10/2018 | Ferro et al. |
| 10,102,309 B2 | 10/2018 | Mckinnon et al. |
| 10,117,658 B2 | 11/2018 | Talbot |
| 10,130,375 B2 | 11/2018 | Yager et al. |
| 10,136,950 B2 | 11/2018 | Schoenefeld |
| 10,136,952 B2 | 11/2018 | Couture et al. |
| 10,172,687 B2 | 1/2019 | Garbus et al. |
| 10,194,991 B2 | 2/2019 | Bonny et al. |
| 10,201,320 B2 | 2/2019 | Saget et al. |
| 10,206,714 B2 | 2/2019 | Van Der Walt et al. |
| 10,206,792 B2 | 2/2019 | Sherman et al. |
| 10,226,261 B2 | 3/2019 | Park et al. |
| 10,226,306 B2 | 3/2019 | Itkowitz et al. |
| 10,231,739 B1 | 3/2019 | Bonutti |
| 10,231,786 B2 | 3/2019 | Ferro et al. |
| 10,238,454 B2 | 3/2019 | Boettner et al. |
| 10,271,954 B2 | 4/2019 | Roach et al. |
| 10,272,569 B2 | 4/2019 | Swarup et al. |
| 10,278,777 B1 | 5/2019 | Lang |
| 10,285,683 B2 | 5/2019 | Plaskos et al. |
| 10,307,269 B2 | 6/2019 | Miller |
| 10,368,947 B2 | 8/2019 | Lang |
| 10,416,624 B2 | 9/2019 | Bly et al. |
| 10,420,611 B2 | 9/2019 | Jaramaz et al. |
| 10,426,556 B2 | 10/2019 | Miga et al. |
| 10,441,366 B2 | 10/2019 | Tabandeh et al. |
| 10,441,438 B1 | 10/2019 | Rahman et al. |
| 10,452,238 B2 | 10/2019 | Nikou et al. |
| 10,456,075 B2 | 10/2019 | Auchinleck et al. |
| 10,456,166 B2 | 10/2019 | Cooper et al. |
| 10,463,242 B2 | 11/2019 | Kesten et al. |
| 10,470,838 B2 | 11/2019 | Epstein et al. |
| 10,492,693 B2 | 12/2019 | Irisawa |
| 10,492,798 B2 | 12/2019 | Metzger |
| 10,548,667 B2 | 2/2020 | Flett et al. |
| 10,555,777 B2 | 2/2020 | Griffiths et al. |
| 10,572,733 B2 | 2/2020 | Wells et al. |
| 10,575,910 B2 | 3/2020 | Itkowitz et al. |
| 10,595,880 B2 | 3/2020 | Otto et al. |
| 10,595,887 B2 | 3/2020 | Shelton et al. |
| 10,595,952 B2 | 3/2020 | Forrest et al. |
| 10,610,310 B2 | 4/2020 | Todd et al. |
| 10,610,315 B2 | 4/2020 | Itkowitz et al. |
| 10,610,316 B2 | 4/2020 | Swarup et al. |
| 10,617,479 B2 | 4/2020 | Itkowitz et al. |
| 10,624,807 B2 | 4/2020 | Itkowitz et al. |
| 10,638,970 B2 | 5/2020 | Obma et al. |
| 10,739,963 B2 | 8/2020 | Nikou et al. |
| 10,765,384 B2 | 9/2020 | Wollowick et al. |
| 2002/0055918 A1 | 5/2002 | Hlathein et al. |
| 2002/0082612 A1 | 6/2002 | Moll et al. |
| 2004/0260301 A1 | 12/2004 | Lionberger et al. |
| 2005/0020941 A1 | 1/2005 | Tarabichi |
| 2005/0113846 A1 | 5/2005 | Carson |
| 2005/0119661 A1 | 6/2005 | Hodgson et al. |
| 2005/0149040 A1 | 7/2005 | Haines et al. |
| 2005/0171545 A1 | 8/2005 | Walsh et al. |
| 2005/0234466 A1 | 10/2005 | Stallings |
| 2005/0251148 A1 | 11/2005 | Friedrich et al. |
| 2006/0015120 A1 | 1/2006 | Richard et al. |
| 2006/0064043 A1 | 3/2006 | Goeggelmann et al. |
| 2006/0200026 A1 | 9/2006 | Wallace et al. |
| 2006/0241405 A1 | 10/2006 | Leitner et al. |
| 2007/0073136 A1 | 3/2007 | Metzger |
| 2007/0123896 A1 | 5/2007 | Wyss et al. |
| 2007/0179626 A1 | 8/2007 | de la Barrera et al. |
| 2008/0004633 A1 | 1/2008 | Arata et al. |
| 2008/0208081 A1 | 8/2008 | Murphy et al. |
| 2008/0249394 A1 | 10/2008 | Giori et al. |
| 2008/0281301 A1 | 11/2008 | Deboer et al. |
| 2008/0281328 A1 | 11/2008 | Lang et al. |
| 2008/0281426 A1 | 11/2008 | Fitz et al. |
| 2010/0063508 A1 | 3/2010 | Borja et al. |
| 2010/0064216 A1 | 3/2010 | Borja et al. |
| 2010/0145344 A1 | 6/2010 | Jordan et al. |
| 2011/0029091 A1 | 2/2011 | Bojarski et al. |
| 2011/0071528 A1 | 3/2011 | Carson |
| 2011/0071530 A1 | 3/2011 | Carson |
| 2011/0304332 A1 | 12/2011 | Mahfouz |
| 2011/0306986 A1 | 12/2011 | Lee et al. |
| 2012/0143084 A1 | 6/2012 | Shoham |
| 2012/0226198 A1 | 9/2012 | Carson |
| 2012/0226481 A1 | 9/2012 | Carson |
| 2013/0072821 A1 | 3/2013 | Odermatt et al. |
| 2013/0085510 A1 | 4/2013 | Stefanchik et al. |
| 2013/0123983 A1* | 5/2013 | Brogardh ............... B25J 9/1692 |
| | | 700/254 |
| 2013/0172905 A1 | 7/2013 | Iorgulescu et al. |
| 2013/0209953 A1 | 8/2013 | Arlinsky et al. |
| 2014/0039520 A1 | 2/2014 | Haider et al. |
| 2014/0073907 A1 | 3/2014 | Kumar et al. |
| 2014/0108983 A1 | 4/2014 | William et al. |
| 2014/0128727 A1 | 5/2014 | Daon et al. |
| 2014/0135791 A1 | 5/2014 | Nikou et al. |
| 2014/0188240 A1 | 7/2014 | Lang et al. |
| 2014/0189508 A1 | 7/2014 | Granchi et al. |
| 2014/0296871 A1 | 10/2014 | Chen et al. |
| 2015/0094736 A1* | 4/2015 | Malackowski ........ A61B 34/30 |
| | | 606/130 |
| 2015/0105782 A1 | 4/2015 | D'Lima et al. |
| 2015/0106024 A1 | 4/2015 | Lightcap et al. |
| 2016/0007836 A1 | 1/2016 | Kikuchi |
| 2016/0022374 A1 | 1/2016 | Haider et al. |
| 2016/0220175 A1 | 8/2016 | Tam et al. |
| 2016/0278868 A1 | 9/2016 | Berend et al. |
| 2016/0338777 A1 | 11/2016 | Penenberg et al. |
| 2017/0014169 A1 | 1/2017 | Dean et al. |
| 2017/0042557 A1 | 2/2017 | Plaskos et al. |
| 2017/0061375 A1 | 3/2017 | Laster et al. |
| 2017/0196571 A1 | 7/2017 | Berend et al. |
| 2017/0252112 A1 | 9/2017 | Crawford et al. |
| 2017/0258532 A1 | 9/2017 | Shalayev et al. |
| 2017/0312099 A1 | 11/2017 | Paszicsnyek |
| 2017/0325973 A1 | 11/2017 | Bonny et al. |
| 2017/0340389 A1 | 11/2017 | Otto et al. |
| 2017/0347922 A1 | 12/2017 | Bhandari |
| 2017/0348008 A1 | 12/2017 | Lavallee et al. |
| 2018/0064496 A1 | 3/2018 | Hladio et al. |
| 2018/0071049 A1 | 3/2018 | Nowatschin et al. |
| 2018/0085135 A1 | 3/2018 | Singh et al. |
| 2018/0085172 A1 | 3/2018 | Bell et al. |
| 2018/0116805 A1 | 5/2018 | Johannaber et al. |
| 2018/0116823 A1 | 5/2018 | Johannaber et al. |
| 2018/0132949 A1 | 5/2018 | Merette et al. |
| 2018/0168750 A1 | 6/2018 | Staunton et al. |

(56) References Cited

U.S. PATENT DOCUMENTS

| | | |
|---|---|---|
| 2018/0168762 A1 | 6/2018 | Scheib et al. |
| 2018/0177512 A1 | 6/2018 | Hogan et al. |
| 2018/0185100 A1* | 7/2018 | Weinstein .............. A61F 2/461 |
| 2018/0199995 A1 | 7/2018 | Odermatt et al. |
| 2018/0214180 A1 | 8/2018 | Theodore et al. |
| 2018/0250078 A1 | 9/2018 | Shochat et al. |
| 2018/0256256 A1 | 9/2018 | May et al. |
| 2018/0317898 A1 | 11/2018 | Plaskos et al. |
| 2018/0338796 A1 | 11/2018 | Yao et al. |
| 2018/0344409 A1 | 12/2018 | Bonny et al. |
| 2018/0368930 A1 | 12/2018 | Esterberg et al. |
| 2019/0000631 A1 | 1/2019 | Blankevoort et al. |
| 2019/0008599 A1 | 1/2019 | Lynch et al. |
| 2019/0066832 A1 | 2/2019 | Kang et al. |
| 2019/0069962 A1 | 3/2019 | Tabandeh et al. |
| 2019/0069963 A1 | 3/2019 | Azizian et al. |
| 2019/0083191 A1 | 3/2019 | Gilhooley et al. |
| 2019/0090952 A1 | 3/2019 | Bonny et al. |
| 2019/0090962 A1 | 3/2019 | Boettner |
| 2019/0099228 A1 | 4/2019 | Keller et al. |
| 2019/0117156 A1 | 4/2019 | Howard et al. |
| 2019/0117407 A1 | 4/2019 | Yang |
| 2019/0122330 A1 | 4/2019 | Saget et al. |
| 2019/0133695 A1 | 5/2019 | Hladio et al. |
| 2019/0147128 A1 | 5/2019 | O'Connor |
| 2019/0175283 A1 | 6/2019 | Bonny et al. |
| 2019/0200900 A1 | 7/2019 | Thelen et al. |
| 2019/0201101 A1 | 7/2019 | Hafez |
| 2019/0201214 A1 | 7/2019 | Miller et al. |
| 2019/0209079 A1 | 7/2019 | Delport |
| 2019/0216520 A1 | 7/2019 | Babak et al. |
| 2019/0223962 A1 | 7/2019 | Roldan et al. |
| 2019/0224016 A1 | 7/2019 | Walker et al. |
| 2019/0240045 A1 | 8/2019 | Couture |
| 2019/0240046 A1 | 8/2019 | Couture |
| 2019/0254756 A1 | 8/2019 | Zhang et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274762 A1 | 9/2019 | Kim et al. |
| 2019/0290198 A1 | 9/2019 | Belson et al. |
| 2019/0311542 A1 | 10/2019 | Douglas et al. |
| 2019/0325386 A1 | 10/2019 | Laster et al. |
| 2019/0336220 A1 | 11/2019 | Hladio et al. |
| 2019/0365481 A1 | 12/2019 | Otto et al. |
| 2019/0374130 A1 | 12/2019 | Bydlon et al. |
| 2019/0380792 A1 | 12/2019 | Poltaretskyi et al. |
| 2019/0388153 A1 | 12/2019 | Running et al. |
| 2019/0388157 A1 | 12/2019 | Shameli et al. |
| 2020/0000400 A1 | 1/2020 | Mckinnon et al. |
| 2020/0015598 A1 | 1/2020 | Hondori et al. |
| 2020/0030036 A1 | 1/2020 | Forstein |
| 2020/0060772 A1 | 2/2020 | Konh et al. |
| 2020/0060773 A1 | 2/2020 | Barral et al. |
| 2020/0100848 A1 | 4/2020 | Zuhars et al. |
| 2020/0113583 A1 | 4/2020 | Philipp et al. |
| 2020/0129311 A1 | 4/2020 | Singh et al. |
| 2020/0305978 A1 | 10/2020 | Tan et al. |
| 2020/0305979 A1 | 10/2020 | Crawford et al. |
| 2020/0323540 A1 | 10/2020 | Kang et al. |
| 2020/0352529 A1 | 11/2020 | Wollowick et al. |
| 2021/0068845 A1 | 3/2021 | Schers et al. |
| 2022/0071720 A1* | 3/2022 | Sexson .................. A61B 34/10 |
| 2023/0146679 A1 | 5/2023 | Lavallée et al. |

FOREIGN PATENT DOCUMENTS

| | | |
|---|---|---|
| EP | 1 226 788 B1 | 10/2006 |
| EP | 1 755 466 B1 | 12/2007 |
| EP | 2 007 291 A2 | 12/2008 |
| EP | 2 156 794 A1 | 2/2010 |
| EP | 2 384 714 A1 | 11/2011 |
| EP | 1 919 390 B1 | 12/2012 |
| EP | 1 841 372 B1 | 9/2017 |
| EP | 3 510 927 A1 | 7/2019 |
| EP | 3 334 383 B1 | 4/2020 |
| WO | WO-95/31148 A1 | 11/1995 |
| WO | WO-2004/070580 A2 | 8/2004 |
| WO | WO-2006/078236 A1 | 7/2006 |
| WO | WO-2007/092841 A1 | 8/2007 |
| WO | WO-2012/082164 A1 | 6/2012 |
| WO | WO-2012/101286 A1 | 8/2012 |
| WO | WO-2015/057814 A1 | 4/2015 |
| WO | WO-2016/146768 A1 | 9/2016 |
| WO | WO-2016/198844 A1 | 12/2016 |
| WO | WO-2017/076886 A1 | 5/2017 |
| WO | WO-2017/108776 A1 | 6/2017 |
| WO | WO-2017/115235 A1 | 7/2017 |
| WO | WO-2017/124043 A1 | 7/2017 |
| WO | WO-2017/147596 A1 | 8/2017 |
| WO | WO-2017/179075 A1 | 10/2017 |
| WO | WO-2018/085694 A1 | 5/2018 |
| WO | WO-2018/085900 A1 | 5/2018 |
| WO | WO-2018/095499 A1 | 5/2018 |
| WO | WO-2018/104704 A1 | 6/2018 |
| WO | WO-2018/161120 A1 | 9/2018 |
| WO | WO-2019/006370 A1 | 1/2019 |
| WO | WO-2019/032828 A2 | 2/2019 |
| WO | WO-2019/068194 A1 | 4/2019 |
| WO | WO-2019/079634 A1 | 4/2019 |
| WO | WO-2019/081915 A1 | 5/2019 |
| WO | WO-2019/135805 A1 | 7/2019 |
| WO | WO-2019/148154 A1 | 8/2019 |
| WO | WO-2019/191722 A1 | 10/2019 |
| WO | WO-2019/224745 A1 | 11/2019 |
| WO | WO-2019/241516 A1 | 12/2019 |
| WO | WO-2019/245849 A1 | 12/2019 |
| WO | WO-2019/245851 A1 | 12/2019 |
| WO | WO-2020/033568 A2 | 2/2020 |
| WO | WO-2020/056443 A1 | 3/2020 |
| WO | WO-2020/065209 A1 | 4/2020 |
| WO | WO-2020/227832 A1 | 11/2020 |

OTHER PUBLICATIONS

International Search Report and Written Opinion for International Application No. PCT/US2021/057024, mailed Feb. 16, 2022, 17 pages.

International Search Report and Written Opinion for International Application No. PCT/US2021/057045, mailed Feb. 14, 2022, 17 pages.

International Search Report and Written Opinion for International Application No. PCT/US2021/057065, mailed Feb. 18, 2022, 19 pages.

* cited by examiner

ROBOTIC SURGICAL SYSTEM WITH MOTORIZED MOVEMENT TO A STARTING POSE FOR A REGISTRATION OR CALIBRATION ROUTINE

CROSS-REFERENCE TO RELATED APPLICATIONS

This application claims the benefit of and priority to U.S. Provisional Patent Application No. 63/107,781 filed Oct. 30, 2020, U.S. Provisional Patent Application No. 63/125,481 filed Dec. 15, 2020, U.S. Provisional Patent Application No. 63/131,654 filed Dec. 29, 2020, and U.S. Provisional Patent Application No. 63/189,508 filed May 17, 2021, the entire disclosures of which are incorporated by reference herein.

BACKGROUND

The present disclosure relates generally to surgical systems for orthopedic surgeries, for example surgical systems that facilitate joint replacement procedures. Joint replacement procedures (arthroplasty procedures) are widely used to treat osteoarthritis and other damage to a patient's joint by replacing portions of the joint with prosthetic components. Joint replacement procedures can include procedures to replace hips, knees, shoulders, or other joints with one or more prosthetic components.

One possible tool for use in an arthroplasty procedure is a robotically-assisted surgical system. A robotically-assisted surgical system typically includes a robotic device that is used to prepare a patient's anatomy to receive an implant, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. Based on the surgical plan, the surgical system guides, controls, or limits movements of the surgical tool during portions of the surgical procedure. Guidance and/or control of the surgical tool serves to assist the surgeon during implementation of the surgical plan. Various features enabling improved planning, improved intra-operative assessments of the patient biomechanics, intraoperative plan adjustments, etc. for use with robotically-assisted surgical systems or other computer-assisted surgical systems may be advantageous.

SUMMARY

Figure 1:
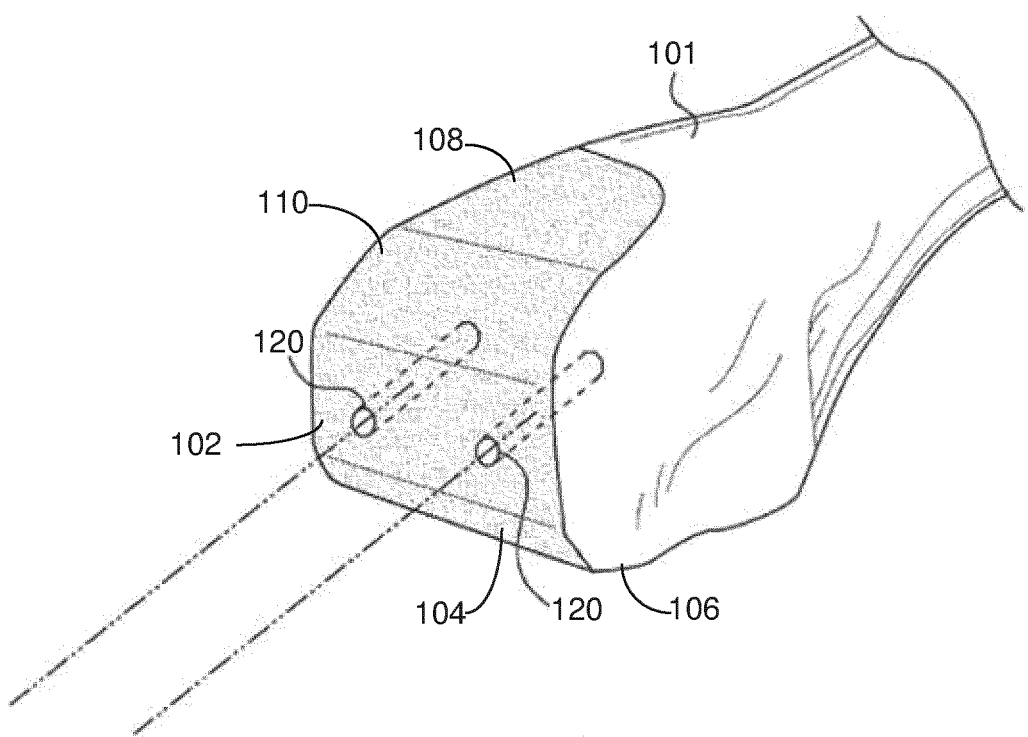
FIG. 1 is a perspective view of a femur prepared to receive an implant component, according to an exemplary embodiment.

One implementation of the present disclosure is a surgical system. The surgical system includes a robotic arm extending from a base, a tracking system configured to track at least one of a first marker attached to a distal end of the robotic arm and a second marker attached to the base, and a controller. The controller is configured to obtain an indication that the base is in position for performing a surgical operation, determine a starting pose for a registration routine for the robotic arm, control the robotic arm to automatically move to the starting pose for the registration routine, and in response to successful automatic movement to the starting pose for the registration routine, perform the registration or calibration routine for the robotic arm.

Another implementation of the present disclosure is a method of controlling a robotic arm mounted on a base. The method includes guiding the base to a position relative to a tracking system and determining a starting pose for a registration or calibration routine for the robotic arm. The starting pose corresponds to an expected position of a surgical field relative to the base. The method includes controlling the robotic arm to automatically move to the starting pose, and, in response to successful automatic movement to the starting pose for the registration or calibration routine, providing the registration or calibration routine for the robotic arm.

Another implementation of the present disclosure is one or more non-transitory computer-readable media storing program instructions that, when executed by one or more processors, cause the one or more processors to perform operations. The operations include obtaining an indication that a base of a robotic device is positioned relative to a tracking system and determining a starting pose for a registration or calibration routine for a robotic arm extending from the base. The starting pose corresponds to an expected position of a surgical field relative to the base. The operations also include controlling the robotic arm to automatically move the robotic arm to the starting pose and, in response to successful automatic movement to the starting pose for the registration or calibration routine, providing the registration or calibration routine for the robotic arm.

DETAILED DESCRIPTION

Presently preferred embodiments of the invention are illustrated in the drawings. An effort has been made to use the same or like reference numbers throughout the drawings to refer to the same or like parts. Although this specification refers primarily to a robotic arm for orthopedic joint replacement, it should be understood that the subject matter described herein is applicable to other types of robotic systems, including those used for non-surgical applications, as well as for procedures directed to other anatomical regions, for example spinal or dental procedures.

Referring now to FIG. 1, a femur 101 as modified during a knee arthroplasty procedure is shown, according to an exemplary embodiment. As shown in FIG. 1, the femur 101 has been modified with multiple planar cuts. In the example shown, the femur 100 has been modified by five substantially planar cuts to create five substantially planar surfaces, namely distal surface 102, posterior chamfer surface 104, posterior surface 106, anterior surface 108, and anterior chamfer surface 110. The planar surfaces may be achieved using a sagittal saw or other surgical tool, for example a surgical tool coupled to a robotic device as in the examples described below. The planar surfaces 102-110 are created such that the planar surfaces 102-110 will mate with corresponding surfaces of a femoral implant component. The positions and angular orientations of the planar surfaces 102-110 may determine the alignment and positioning of the implant component. Accordingly, operating a surgical tool to create the planar surfaces 102-110 with a high degree of accuracy may improve the outcome of a joint replacement procedure.

As shown in FIG. 1, the femur 101 has also been modified to have a pair of pilot holes 120. The pilot holes 120 extend into the femur 101 and are created such that the pilot holes 120 can receive a screw, a projection extending from a surface of an implant component, or other structure configured to facilitate coupling of an implant component to the femur 101. The pilot holes 120 may be created using a drill, spherical burr, or other surgical tool as described below. The pilot holes 120 may have a pre-planned position, orientation, and depth, which facilitates secure coupling of the implant component to the bone in a desired position and orientation. In some cases, the pilot holes 120 are planned to intersect with higher-density areas of a bone and/or to avoid other implant components and/or sensitive anatomical features. Accordingly, operating a surgical tool to create the pilot holes 120 with a high degree of accuracy may improve the outcome of a joint replacement procedure.

A tibia may also be modified during a joint replacement procedure. For example, a planar surface may be created on the tibia at the knee joint to prepare the tibia to mate with a tibial implant component. In some embodiments, one or more pilot holes or other recess (e.g., fin-shaped recess) may also be created in the tibia to facilitate secure coupling of an implant component tot eh bone.

In some embodiments, the systems and methods described herein provide robotic assistance for creating the planar surfaces 102-110 and the pilot holes 120 at the femur, and/or a planar surface and/or pilot holes 120 or other recess on a tibia. It should be understood that the creation of five planar cuts and two cylindrical pilot holes as shown in FIG. 1 is an example only, and that the systems and methods described herein may be adapted to plan and facilitate creation of any number of planar or non-planar cuts, any number of pilot holes, any combination thereof, etc., for preparation of any bone and/or joint in various embodiments. For example, in a hip or shoulder arthroplasty procedure, a spherical burr may be used in accordance with the systems and methods herein to ream a curved surface configured to receive a curved implant cup. Furthermore, in other embodiments, the systems and methods described herein may be used to facilitate placement an implant component relative to a bone (e.g., to facilitate impaction of cup implant in a hip arthroplasty procedure). Many such surgical and non-surgical implementations are within the scope of the present disclosure.

The positions and orientations of the planar surfaces 102-110, pilot holes 120, and any other surfaces or recesses created on bones of the knee joint can affect how well implant components mate to the bone as well as the resulting biomechanics for the patient after completion of the surgery. Tension on soft tissue can also be affected. Accordingly, systems and methods for planning the cuts which create these surfaces, facilitating intra-operative adjustments to the surgical plan, and providing robotic-assistance or other guidance for facilitating accurate creation of the planar surfaces 102-110, other surfaces, pilot holes 120, or other recesses can make surgical procedures easier and more efficient for healthcare providers and improve surgical outcomes.

Figure 2:
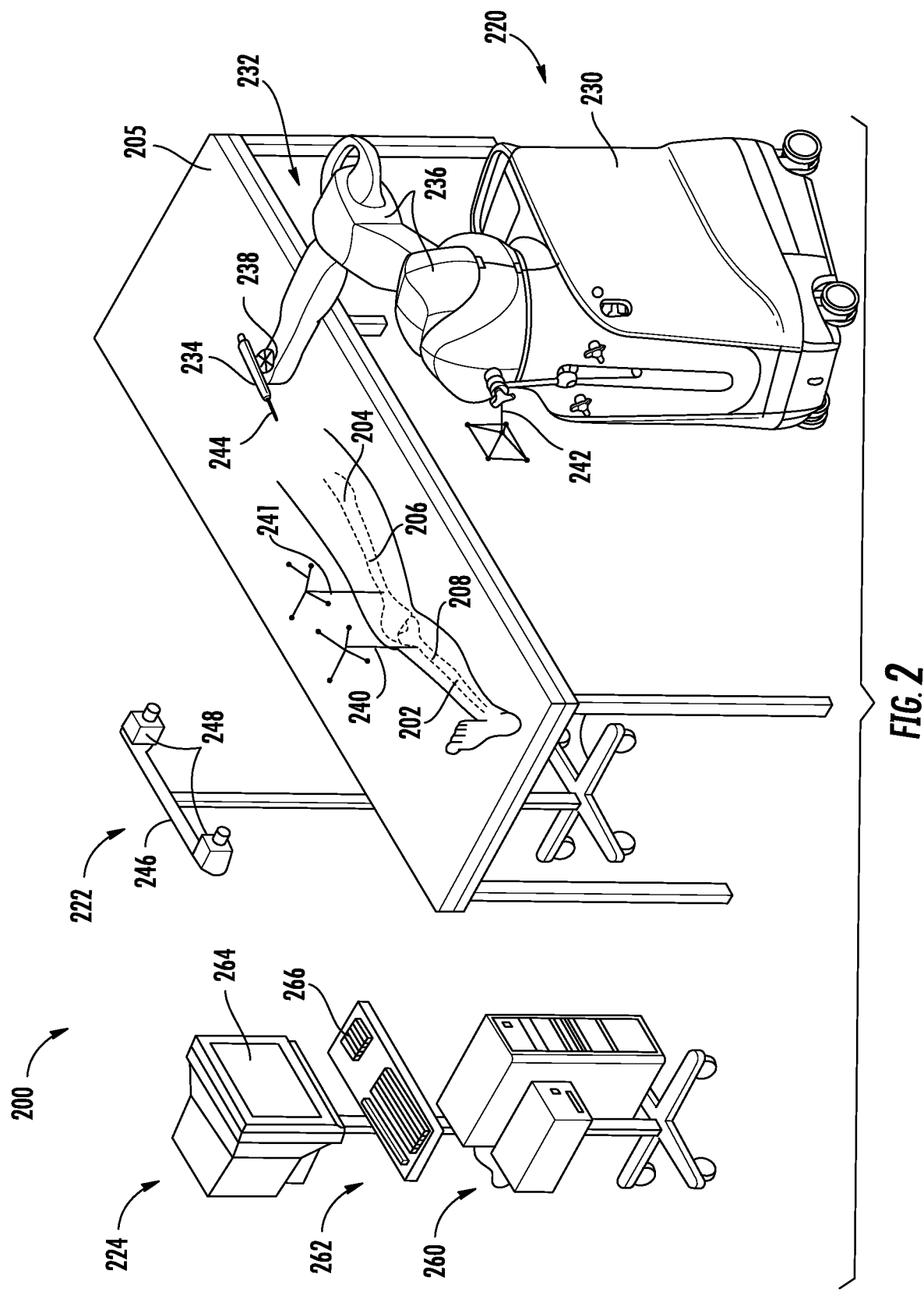
FIG. 2 is an illustration of a surgical system, according to an exemplary embodiment.

Referring now to FIG. 2, a surgical system 200 for orthopedic surgery is shown, according to an exemplary embodiment. In general, the surgical system 200 is configured to facilitate the planning and execution of a surgical plan, for example to facilitate a joint-related procedure. As shown in FIG. 2, the surgical system 200 is set up to treat a leg 202 of a patient 204 sitting or lying on table 205. In the illustration shown in FIG. 2, the leg 202 includes femur 206 (e.g., femur 101 of FIG. 1) and tibia 208, between which a prosthetic knee implant is to be implanted in a total knee arthroscopy procedure. In other scenarios, the surgical system 200 is set up to treat a hip of a patient, i.e., the femur and the pelvis of the patient. Additionally, in still other scenarios, the surgical system 200 is set up to treat a shoulder of a patient, i.e., to facilitate replacement and/or augmentation of components of a shoulder joint (e.g., to facilitate placement of a humeral component, a glenoid component, and a graft or implant augment). Various other anatomical regions and procedures are also possible.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 220 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 224, may autonomously complete the series of femoral cuts mentioned above without direct human intervention.

The robotic device 220 includes a base 230, a robotic arm 232, and a surgical tool 234, and is communicably coupled to the computing system 224 and the tracking system 222. The base 230 provides a moveable foundation for the robotic arm 232, allowing the robotic arm 232 and the surgical tool 234 to be repositioned as needed relative to the patient 204 and the table 205. The base 230 may also contain power systems, computing elements, motors, and other electronic or mechanical system necessary for the functions of the robotic arm 232 and the surgical tool 234 described below.

The robotic arm 232 is configured to support the surgical tool 234 and provide a force as instructed by the computing system 224. In some embodiments, the robotic arm 232 allows a user to manipulate the surgical tool and provides force feedback to the user. In such an embodiment, the robotic arm 232 includes joints 236 and mount 238 that include motors, actuators, or other mechanisms configured to allow a user to freely translate and rotate the robotic arm 232 and surgical tool 234 through allowable poses while providing force feedback to constrain or prevent some movements of the robotic arm 232 and surgical tool 234 as instructed by computing system 224. As described in detail below, the robotic arm 232 thereby allows a surgeon to have full control over the surgical tool 234 within a control object while providing force feedback along a boundary of that object (e.g., a vibration, a force preventing or resisting penetration of the boundary). In some embodiments, the robotic arm is configured to move the surgical tool to a new pose automatically without direct user manipulation, as instructed by computing system 224, in order to position the robotic arm as needed and/or complete certain surgical tasks, including, for example, cuts in a femur 206.

The surgical tool 234 is configured to cut, burr, grind, drill, partially resect, reshape, and/or otherwise modify a bone. The surgical tool 234 may be any suitable tool, and may be one of multiple tools interchangeably connectable to robotic device 220. For example, as shown in FIG. 2 the surgical tool 234 includes a spherical burr 244. In other examples, the surgical tool may also be a sagittal saw, for example with a blade aligned parallel with a tool axis or perpendicular to the tool axis. The surgical tool may also be a drill, for example with a rotary bit aligned parallel with a tool axis or perpendicular to the tool axis. The surgical tool 234 may also be a holding arm or other support configured to hold an implant component (e.g., cup 28a, implant augment, etc.) in position while the implant component is screwed to a bone, adhered (e.g., cemented) to a bone or other implant component, or otherwise installed in a preferred position. In some embodiments, the surgical tool 234 is an impaction tool configured to provide an impaction force to a cup implant to facilitate fixation of the cup implant to a pelvis in a planned location and orientation.

Tracking system 222 is configured track the patient's anatomy (e.g., femur 206 and tibia 208) and the robotic device 220 (i.e., surgical tool 234 and/or robotic arm 232) to enable control of the surgical tool 234 coupled to the robotic arm 232, to determine a position and orientation of modifications or other results made by the surgical tool 234, and allow a user to visualize the bones (e.g., femur 206, the tibia 208, pelvis, humerus, scapula, etc. as applicable in various procedures), the surgical tool 234, and/or the robotic arm 232 on a display of the computing system 224. The tracking system 222 can also be used to collect biomechanical measurements relating to the patient's anatomy, assess joint gap distances, identify a hip center point, assess native or corrected joint deformities, or otherwise collect information relating to the relative poses of anatomical features. More particularly, the tracking system 222 determines a position and orientation (i.e., pose) of objects (e.g., surgical tool 234, femur 206) with respect to a coordinate frame of reference and tracks (i.e., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials attachable to surgical tool 234, and a detection device 246 configured to detect the three-dimensional position of fiducials (i.e., markers on fiducial trees 240-242). Fiducial trees 240, 241 may be coupled to other bones as suitable for various procedures (e.g., pelvis and femur in a hip arthroplasty procedure). Detection device 246 may be an optical detector such as a camera or infrared sensor. The fiducial trees 240-242 include fiducials, which are markers configured to show up clearly to the optical detector and/or be easily detectable by an image processing system using data from the optical detector, for example by being highly reflective of infrared radiation (e.g., emitted by an element of tracking system 222). In some embodiments, the markers are active light emitting diodes. A stereoscopic arrangement of cameras 248 on detection device 246 allows the position of each fiducial to be determined in 3D-space through a triangulation approach in the example shown. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (i.e., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical tool 234 relative to a patient's anatomical feature, for example femur 206, as the surgical tool 234 is used to modify the anatomical feature or otherwise facilitate the surgical procedure. Additionally, using the tracking system 222 of FIG. 2 or some other approach to surgical navigation and tracking, the surgical system 200 can determine the relative poses of the tracked bones.

The computing system 224 is configured to create a surgical plan, control the robotic device 220 in accordance with the surgical plan to make one or more bone modifications and/or facilitate implantation of one or more prosthetic components. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer code for executing (e.g., by the processing circuit 260 and/or processor) one or more processes described herein.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed. The imaging data may be created using any suitable medical imaging technique to image the relevant anatomical feature, including computed tomography (CT), magnetic resonance imaging (MM), and/or ultrasound. The imaging data is then segmented (i.e., the regions in the imaging corresponding to different anatomical features are distinguished) to obtain the virtual bone model. For example, MM-based scan data of a joint can be segmented to distinguish bone from surrounding ligaments, cartilage, previously-implanted prosthetic components, and other tissue to obtain a three-dimensional model of the imaged bone.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.). In some embodiments, the surgical plan may be generated and/or modified based on distraction force measurements collected intraoperatively.

The preoperative surgical plan includes the desired cuts, holes, surfaces, burrs, or other modifications to a patient's anatomy to be made using the surgical system 200. For example, for a total knee arthroscopy procedure, the preoperative plan may include the cuts necessary to form, on a femur, a distal surface, a posterior chamfer surface, a posterior surface, an anterior surface, and an anterior chamfer surface in relative orientations and positions suitable to be mated to corresponding surfaces of the prosthetic to be joined to the femur during the surgical procedure, as well as cuts necessary to form, on the tibia, surface(s) suitable to mate to the prosthetic to be joined to the tibia during the surgical procedure. As another example, the preoperative plan may include the modifications necessary to create holes (e.g., pilot holes 120) in a bone. As another example, in a hip arthroplasty procedure, the surgical plan may include the burr necessary to form one or more surfaces on the acetabular region of the pelvis to receive a cup and, in suitable cases, an implant augment. Accordingly, the processing circuit 260 may receive, access, and/or store a model of the prosthetic to facilitate the generation of surgical plans. In some embodiments, the processing circuit facilitate intraoperative modifications tot eh preoperative plant.

The processing circuit 260 is further configured to generate a control object for the robotic device 220 in accordance with the surgical plan. The control object may take various forms according to the various types of possible robotic devices (e.g., haptic, autonomous). For example, in some embodiments, the control object defines instructions for the robotic device to control the robotic device to move within the control object (i.e., to autonomously make one or more cuts of the surgical plan guided by feedback from the tracking system 222). In some embodiments, the control object includes a visualization of the surgical plan and the robotic device on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical tool 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone. A curved haptic object may represent a resulting surface of a bone as modified to receive a cup implant and/or implant augment. A line haptic object may correspond to a pilot hole to be made in a bone to prepare the bone to receive a screw or other projection.

In an embodiment where the robotic device 220 is a haptic device, the processing circuit 260 is further configured to generate a virtual tool representation of the surgical tool 234. The virtual tool includes one or more haptic interaction points (HIPs), which represent and are associated with locations on the physical surgical tool 234. In an embodiment in which the surgical tool 234 is a spherical burr (e.g., as shown in FIG. 2), a HIP may represent the center of the spherical burr. Where one HIP is used to virtually represent a surgical tool, the HIP may be referred to herein as a tool center point (TCP). If the surgical tool 234 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to an "HIP" are deemed to also include references to "one or more HIPs." As described below, relationships between HIPs and haptic objects enable the surgical system 200 to constrain the surgical tool 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010, 180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 234 to a virtual tool representation of the surgical tool 234, so that the surgical system 200 can determine and monitor the pose of the surgical tool 234 relative to the patient (i.e., to femur 206). Registration of allows for accurate navigation, control, and/or force feedback during the surgical procedure.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical tool 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 to minimize the need to track and process motion of the femur 206.

For embodiments where the robotic device 220 is a haptic device, the surgical system 200 is configured to constrain the surgical tool 234 based on relationships between HIPs and haptic objects. That is, when the processing circuit 260 uses data supplied by tracking system 222 to detect that a user is manipulating the surgical tool 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical tool 234. In general, the term "constrain," as used herein, is used to describe a tendency to restrict movement. However, the form of constraint imposed on surgical tool 234 depends on the form of the relevant haptic object. A haptic object may be formed in any desirable shape or configuration. As noted above, three exemplary embodiments include a line, plane, or three-dimensional volume. In one embodiment, the surgical tool 234 is constrained because a HIP of surgical tool 234 is restricted to movement along a linear haptic object. In another embodiment, the haptic object is a three-dimensional volume and the surgical tool 234 may be constrained by substantially preventing movement of the HIP outside of the volume enclosed by the walls of the three-dimensional haptic object. In another embodiment, the surgical tool 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface on the femur 206 in order to confine the surgical tool 234 substantially to the plane needed to carry out the planned distal cut.

For embodiments where the robotic device 220 is an autonomous device, the surgical system 200 is configured to autonomously move and operate the surgical tool 234 in accordance with the control object. For example, the control object may define areas relative to the femur 206 for which a cut should be made. In such a case, one or more motors, actuators, and/or other mechanisms of the robotic arm 232 and the surgical tool 234 are controllable to cause the surgical tool 234 to move and operate as necessary within the control object to make a planned cut, for example using tracking data from the tracking system 222 to allow for closed-loop control.

Figure 3:
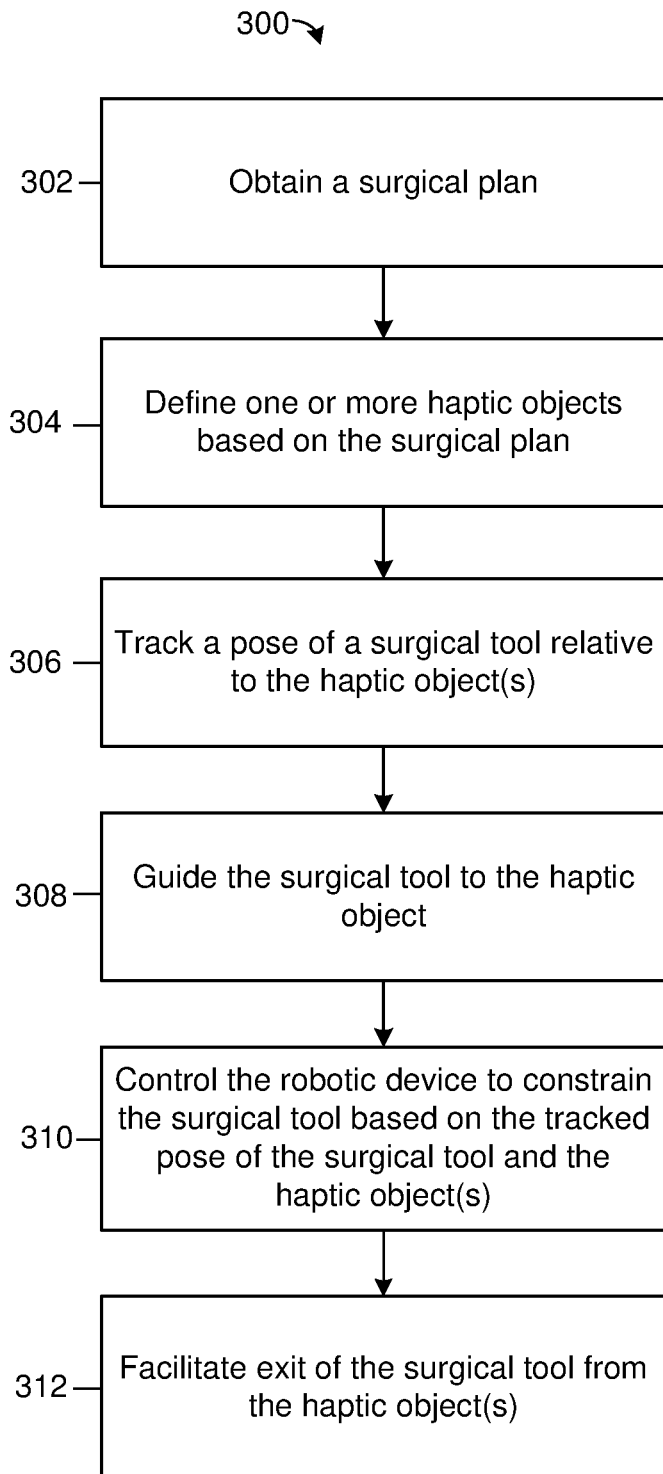
FIG. 3 is a flowchart of a first process that can be executed by the surgical system of FIG. 2, according to an exemplary embodiment.

Referring now to FIG. 3, a flowchart of a process 300 that can be executed by the surgical system 200 of FIG. 2 is shown, according to an exemplary embodiment. Process 300 may be adapted to facilitate various surgical procedures, including total and partial joint replacement surgeries.

At step 302, a surgical plan is obtained. The surgical plan (e.g., a computer-readable data file) may define a desired outcome of bone modifications, for example defined based on a desired position of prosthetic components relative to the patient's anatomy. For example, in the case of a knee arthroplasty procedure, the surgical plan may provide planned positions and orientations of the planar surfaces 102-110 and the pilot holes 120 as shown in FIG. 1. The surgical plan may be generated based on medical imaging, 3D modeling, surgeon input, etc.

At step 304, one or more control boundaries, such as haptic objects, are defined based on the surgical plan. The one or more haptic objects may be one-dimensional (e.g., a line haptic), two dimensional (i.e., planar), or three dimensional (e.g., cylindrical, funnel-shaped, curved, etc.). The haptic objects may represent planned bone modifications (e.g., a haptic object for each of the planar surfaces 102-110 and each of the pilot holes 120 shown in FIG. 1), implant components, surgical approach trajectories, etc. defined by the surgical plan. The haptic objects can be oriented and positioned in three-dimensional space relative to a tracked position of a patient's anatomy.

At step 306, a pose of a surgical tool is tracked relative to the haptic object(s), for example by the tracking system 222 described above. In some embodiments, one point on the surgical tool is tracked. In other embodiments, (e.g., in the example of FIGS. 4-5) two points on the surgical tool are tracked, for example a tool center point (TCP) at a tip/effective end of the surgical tool and a second interaction point (SIP) positioned along a body or handle portion of the surgical tool. In other embodiments, three or more points on the surgical tool are tracked. A pose of the surgical tool is ascertained relative to a coordinate system in which the one or more haptic objects are defined and, in some embodiments, in which the pose of one or more anatomical features of the patient is also tracked.

At step 308, the surgical tool is guided to the haptic object(s). For example, the display 264 of the surgical system 200 may display a graphical user interface instructing a user on how (e.g., which direction) to move the surgical tool and/or robotic device to bring the surgical tool to a haptic object. As another example, the surgical tool may be guided to a haptic object using a collapsing haptic boundary as described in U.S. Pat. No. 9,289,264, the entire disclosure of which is incorporated by reference herein. As another example, the robotic device may be controlled to automatically move the surgical tool to a haptic object.

In an embodiment where the robotic device is controlled to automatically move the surgical tool to the haptic object (referred to as motorized alignment or automated alignment), the robotic device may be controlled so that a duration of the alignment is bounded by preset upper and lower time thresholds. That is, across various instances of process 300 and multiple procedures, automated alignment in step 308 may be configured to always take between a first amount of time (the lower time threshold) and a second amount of time (the upper time threshold). The lower time threshold may be selected such that the robotic device moves over a long enough duration to be perceived as well-controlled and to minimize collision or other risks associated with high speed. The upper time threshold may be selected such that the robotic device moves over a short enough duration to avoid user impatience and provide improved usability. For example, the upper time threshold hold may be approximately five seconds in an example where the lower time thresholds is approximately three seconds. In other embodiments, a single duration setpoint is used (e.g., four seconds). Step 308 can include optimizing a path for the robotic device such that the step 308 ensures successful alignment to the haptic object while also satisfying the upper and lower time thresholds or duration setpoint.

At step 310, the robotic device is controlled to constrain movement of the surgical tool based on the tracked pose of the surgical tool and the poses of one or more haptic objects. The constraining of the surgical tool may be achieved as described above with reference to FIG. 2.

At step 312, exit of the surgical tool from the haptic object(s) is facilitated, i.e., to release the constraints of a haptic object. For example, in some embodiments, the robotic device is controlled to allow the surgical tool to exit a haptic object along an axis of the haptic object. In some embodiments, the surgical tool may be allowed to exit the haptic object in a pre-determined direction relative to the haptic object. The surgical tool may thereby be removed from the surgical field and the haptic object to facilitate subsequent steps of the surgical procedure. Additionally, it should be understood that, in some cases, the process 300 may return to step 308 where the surgical tool is guided to the same or different haptic object after exiting a haptic object at step 312.

Process 300 may thereby be executed by the surgical system 200 to facilitate a surgical procedure. Features of process 300 are shown in FIGS. 4-8 below according to some embodiments, and such features can be combined in various combinations in various embodiments and/or based on settings selected for a particular procedure. Furthermore, it should be understood that the features of FIGS. 4-8 may be provided while omitting some or all other steps of process 300. All such possibilities are within the scope of the present disclosure.

Figure 4:
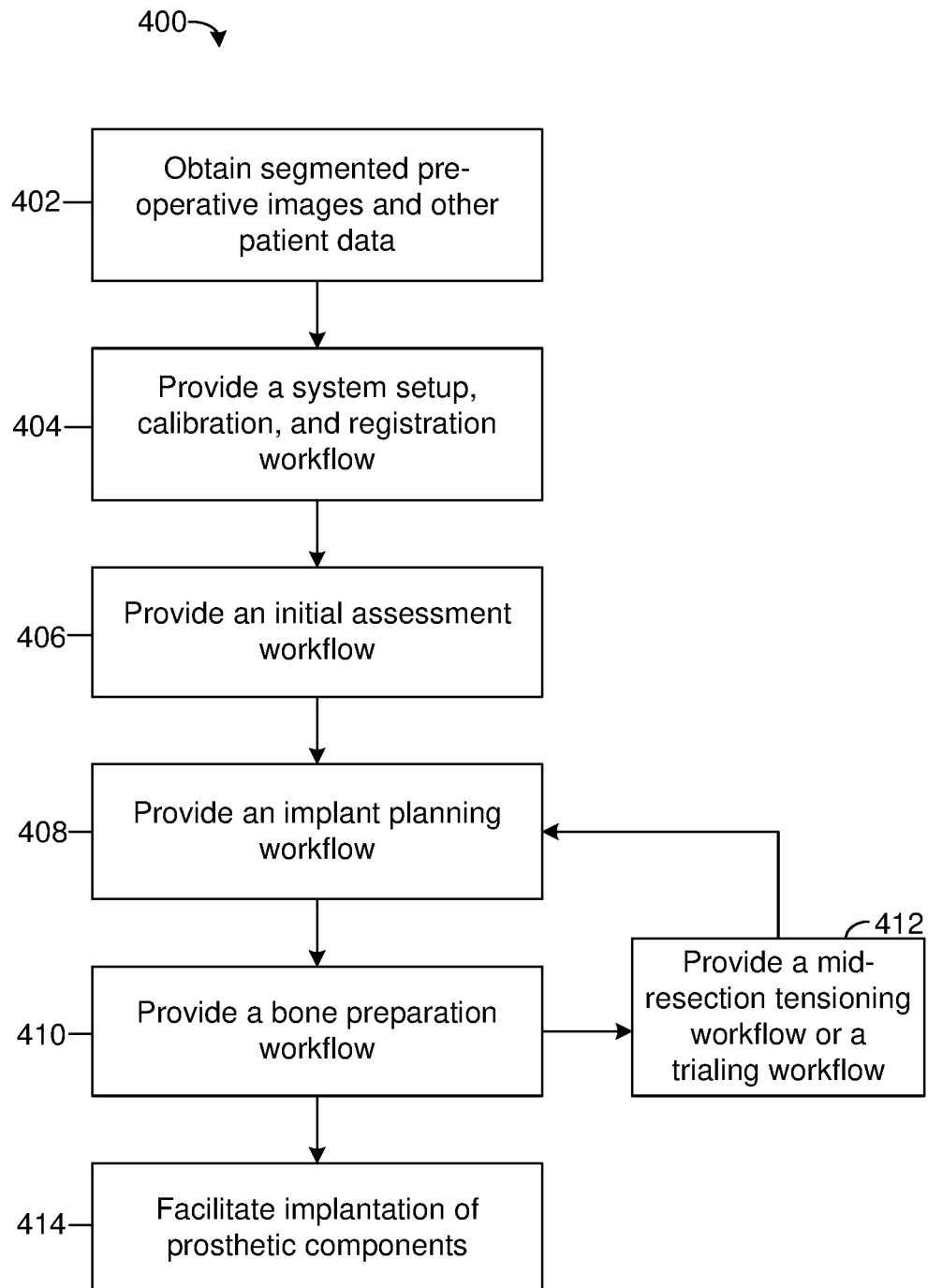
FIG. 4 is a flowchart of a second process that can be executed by the surgical system of FIG. 2, according to an exemplary embodiment.

Referring now to FIG. 4, a flowchart of a process 400 for facilitating surgical planning and guidance is shown, according to an exemplary embodiment. The process 400 may be executed by the surgical system 200 of FIG. 2, in some embodiments. In some cases, the process 300 is executed as part of executing the process 400.

At step 402, segmented pre-operative images and other patient data are obtained, for example by the surgical system 200. For example, segmented pre-operative CT images or MRI images may be received at the computing system 224 from an external server. In some cases, pre-operative images of a patient's anatomy are collected using an imaging device and segmented by a separate computing system and/or with manual user input to facilitate segmentation. In other embodiments, unsegmented pre-operative images are received at the computing system 224 and the computing system 224 is configured to automatically segment the images. The segmented pre-operative images can show the geometry, shape, size, density, and/or other characteristics of bones of a joint which is to be operated on in a procedure performed using process 400.

Other patient data can also be obtained at step 402. For example, the computing system 224 may receive patient information from an electronic medical records system. As another example, the computing system 224 may accept user input of patient information. The other patient data may include a patient's name, identification number, biographical information (e.g., age, weight, etc.), other health conditions, etc. In some embodiments, the patient data obtained at step 402 includes information specific to the procedure to be performed and the relevant pre-operative diagnosis. For example, the patient data may indicate which joint the procedure will be performed on (e.g., right knee, left knee). The patient data may indicate a diagnosed deformity, for example indicating whether a knee joint was diagnosed as having a varus deformity or a valgus deformity. This or other data that may facilitate the surgical procedure may be obtained at step 402.

At step 404, a system setup, calibration, and registration workflow is provided, for example by the surgical system 200. The system setup, calibration, and registration workflows may be configured to prepare the surgical system 200 for use in facilitating a surgical procedure. For example, at step 404, the computer system 224 may operate to provide graphical user interfaces that include instructions for performing system setup, calibration, and registrations steps. The computer system 224 may also cause the tracking system 222 to collect tracking data and control the robotic device 220 to facilitate system setup, calibration, and/or registration. The computer system 224 may also receiving tracking data from the tracking system 222 and information from the computer system 224 and use the received information and data to calibrate the robotic device 220 and define various geometric relationships between tracked points (e.g., fiducials, markers), other components of the surgical system 200 (e.g., robotic arm 232, surgical tool 234, probe), and virtual representations of anatomical features (e.g., virtual bone models).

The system setup workflow provided at step 404 may include guiding the robotic device 220 to a position relative to a surgical table and the patient which will be suitable for completing an entire surgical procedure without repositioning the robotic device 220. For example, the computer system 224 may generate and provide a graphical user interface configured to provide instructions for moving a portable cart of the robotic device 220 into a preferred position. In some embodiments, the robotic device 220 can be tracked to determine whether the robotic device 220 is properly positioned. Once the cart is positioned, in some embodiments the robotic device 220 is controlled to automatically position the robotic arm 232 in a pose suitable for initiation of calibration and/or registration workflows.

The calibration and registration workflows provided at step 404 may include generating instructions for a user to perform various calibration and registration tasks while operating the tracking system 222 to generate tracking data. The tracking data can then be used to calibrate the tracking system 222 and the robotic device 220 and to register the first fiducial tree 240, second fiducial tree 241, and third fiducial tree 242 relative to the patient's anatomical features, for example by defining geometric relationships between the fiducial trees 240-242 and relevant bones of the patient in the example of FIG. 2. The registration workflow may include tracking a probe used to touch various points on the bones of a joint. In some embodiments, providing the registration workflow may include providing instructions to couple a checkpoint (e.g., a screw or pin configured to be contacted by a probe) to a bone and tracking a probe as the probe contacts the checkpoint and as the probe is used to paint (i.e., move along, touch many points along) one or more surfaces of the bone. The probe can be moved and tracked in order to collect points in or proximate the joint to be operated upon as well as at other points on the bone (e.g., at ankle or hip for a knee surgery).

In some embodiments, providing the registration workflow includes generating instructions to move the patient's leg to facilitate collection of relevant tracking data that can be used to identify the location of a biomechanical feature, for example a hip center point. Providing the registration workflow can include providing audio or visual feedback indicating whether the leg was moved in the proper manner to collect sufficient tracking data. Various methods and approaches for registration and calibration can be used in various embodiments. Step 404 may include steps performed before or after an initial surgical incision is made in the patient's skin to initiate the surgical procedure.

At step 406, an initial assessment workflow is provided, for example by the surgical system 200. The initial assessment workflow provides an initial assessment of the joint to be operated upon based on tracked poses of the bones of the joint. For example, the initial assessment workflow may include tracking relative positions of a tibia and a femur using data from the tracking system while providing real-time visualizations of the tibia and femur via a graphical user interface. The computing system 224 may provide instructions via the graphical user interface to move the tibia and femur to different relative positions (e.g., different degrees of flexion) and to exert different forces on the joint (e.g., a varus or valgus force). In some embodiments, the initial assessment workflow includes determine, by the surgical system 200 and based on data from the tracking system 222, whether the patient's joint has a varus or valgus deformity, and, in some embodiments, determining a magnitude of the deformity. In some embodiments, the initial assessment workflow may include collecting data relating to native ligament tension or native gaps between bones of the joint. In some embodiments, the initial assessment workflow may include displaying instructions to exert a force on the patient's leg to place the joint in a corrected state corresponding to a desired outcome for a joint arthroplasty procedure, and recording the relative poses of the bones and other relevant measurements while the joint is in the corrected state. The initial assessment workflow thereby results in collection of data that may be useful for the surgical system 200 or a surgeon in later steps of process 400.

At step 408, an implant planning workflow is provided, for example by the surgical system 200. The implant planning workflow is configured to facilitate users in planning implant placement relative to the patient's bones and/or planning bone cuts or other modifications for preparing bones to receive implant components. Step 408 may include generating, for example by the computing system 324, three-dimensional computer models of the bones of the joint (e.g., a tibia model and a femur model) based on the segmented medical images received at step 402. Step 408 may also include obtaining three-dimensional computer models of prosthetic components to be implanted at the joint (e.g., a tibial implant model and a femoral implant model). A graphical user interface can be generated showing multiple views of the three-dimensional bone models with the three-dimensional implant models shown in planned positions relative to the three-dimensional bone models. Providing the implant planning workflow can include enabling the user to adjust the position and orientation of the implant models relative to the bone models. Planned cuts for preparing the bones to allow the implants to be implanted at the planned positions can then be automatically based on the positioning of the implant models relative to the bone models.

The graphical user interface can include data and measurements from pre-operative patient data (e.g., from step 402) and from the initial assessment workflow (step 406) and/or related measurements that would result from the planned implant placement. The planned measurements (e.g., planned gaps, planned varus/valgus angles, etc.) can be calculated based in part on data collected via the tracking system 222 in other phases of process 400, for example from initial assessment in step 406 or trialing or tensioning workflows described below with reference to step 412.

The implant planning workflow may also include providing warnings (alerts, notifications) to users when an implant plan violates various criteria. In some cases, the criteria can be predefined, for example related to regulatory or system requirements that are constant for all surgeons and/or for all patients. In other embodiments, the criteria may be related to surgeon preferences, such that the criteria for triggering a warning can be different for different surgeons. In some cases, the computing system 224 can prevent the process 400 from moving out of the implant planning workflow when one or more of certain criteria are not met.

The implant planning workflow provided at step 408 thereby results in planned cuts for preparing a joint to receive prosthetic implant components. In some embodiments, the planned cuts include a planar tibial cut and multiple planar femoral cuts, for example as described above with reference to FIG. 1. The planned cuts can be defined relative to the virtual bone models used in the implant planning workflow at step 408. Based on registration processes from step 404 which define a relationship between tracked fiducial markers and the virtual bone models, the positions and orientations of the planned cuts can also be defined relative to the tracked fiducial markers, (e.g., in a coordinate system used by the tracking system 222). The surgical system 200 is thereby configured to associate the planned cuts output from step 408 with corresponding planes or other geometries in real space.

At step 410, a bone preparation workflow is provided, for example by the surgical system 200. The bone preparation workflow includes guiding execution of one or more cuts or other bone modifications based on the surgical plan created at step 408. For example, as explained in detail above with reference to FIGS. 2-3, the bone preparation workflow may include providing haptic feedback which constrains the surgical tool 234 to a plane associated with a planned cut to facilitate use of the surgical tool 234 to make that planned cut. In other embodiments, the bone preparation workflow can include automatically controlling the robotic device 220 to autonomously make one or more cuts or other bone modifications to carry out the surgical plan created at step 408. In other embodiments, the bone preparation workflow comprises causing the robotic device 220 to hold a cutting guide, drill guide, jig, etc. in a substantially fixed position that allows a separate surgical tool to be used to execute the planned cut while being confined by the cutting guide, drill guide, jig, etc. The bone preparation workflow can thus include control of a robotic device in accordance with the surgical plan.

The bone preparation workflow at step 410 can also include displaying graphical user interface elements configured to guide a surgeon in completing one or more planned cuts. For example, the bone preparation workflow can include tracking the position of a surgical tool relative to a plane or other geometry associated with a planned cut and relative to the bone to be cut. In this example, the bone preparation workflow can include displaying, in real-time, the relative positions of the surgical tool, cut plane or other geometry, and bone model. In some embodiments, visual, audio, or haptic warnings can be provided to indicate completion or start of an event or step of the procedure, entry or exit from a state or virtual object, interruptions to performance of the planned cut, deviation from the planned cut, or violation of other criteria relating to the bone preparation workflow.

In some embodiments, step 410 is provided until all bone cuts planned at step 408 are complete and the bones are ready to be coupled to the implant components. In other embodiments, for example as shown in FIG. 4, a first iteration of step 410 can include performing only a portion of the planned cuts. For example, in a total knee arthroplasty procedure, a first iteration of step 410 can include making a tibial cut to provide a planar surface on the tibia without modifying the femur in the first iteration of step 410.

Following an iteration of the bone preparation workflow at step 410, the process 400 can proceed to step 412. At step 412 a mid-resection tensioning workflow or a trialing workflow is provided, for example by the surgical system 200. The mid-resection tensioning workflow is provided when less than all of the bone resection has been completed. The trialing workflow is provided when all resections have been made and/or bones are otherwise prepared to be temporarily coupled to trial implants. The mid-resection tensioning workflow and the trialing workflow at step 412 provide for collection of intraoperative data relating to relative positions of bones of the joint using the tracking system 222 including performing gap measurements or other tensioning procedures that can facilitate soft tissue balancing and/or adjustments to the surgical plan.

For example, step 412 may include displaying instructions to a user to move the joint through a range of motion, for example from flexion to extension, while the tracking system 222 tracks the bones. In some embodiments, gap distances between bones are determined from data collected by the tracking system 222 as a surgeon places the joint in both flexion and extension. In some embodiments, soft tissue tension or distraction forces are measured. Because one or more bone resections have been made before step 412 and soft tissue has been affected by the procedure, the mechanics of the joint may be different than during the initial assessment workflow of step 402 and relative to when the pre-operative imaging was performed. Accordingly, providing for intra-operative measurements in step 412 can provide information to a surgeon and to the surgical system 200 that was not available pre-operatively and which can be used to help fine tune the surgical plan.

From step 412, the process 400 returns to step 408 to provide the implant planning workflow again, now augmented with data collected during a mid-resection or trialing workflow at step 412. For example, planned gaps between implants can be calculated based on the intraoperative measurements collected at step 414, the planned position of a tibial implant relative to a tibia, and the planned position of a femoral implant relative to a femur. The planned gap values can then be displayed in an implant planning interface during step 408 to allow a surgeon to adjust the planned implant positions based on the calculated gap values. In various embodiments, a second iteration of step 408 to provide the implant planning workflow incorporates various data from step 412 in order to facilitate a surgeon in modifying and fine-tuning the surgical plan intraoperatively.

Steps 408, 410, and 412 can be performed multiple times to provide for intra-operative updates to the surgical plan based on intraoperative measurements collected between bone resections. For example, in some cases, a first iteration of steps 408, 410, and 412 includes planning a tibial cut in step 408, executing the planned tibial cut in step 410, and providing a mid-resection tensioning workflow in step 414. In this example, a second iteration of steps 408, 410, and 412 can include planning femoral cuts using data collected in the mid-resection tensioning workflow in step 408, executing the femoral cuts in step 410, and providing a trialing workflow in step 412. Providing the trialing workflow can include displaying instructions relating to placing trial implants on the prepared bone surfaces, and, in some embodiments, verifying that the trial implants are positioned in planned positions using the tracking system 222. Tracking data can be collected in a trialing workflow in step 412 relating to whether the trial implants are placed in acceptable positions or whether further adjustments to the surgical plan are needed by cycling back to step 408 and making further bone modifications in another iteration of step 410.

In some embodiments, executing process 400 can include providing users with options to jump between steps of the process 400 to enter a desired workflow. For example, a user can be allowed to switch between implant planning and bone preparation on demand. In other embodiments, executing process 400 can include ensuring that a particular sequence of steps of process 400 are followed. In various embodiments, any number of iterations of the various steps can be performed until a surgeon is satisfied that the bones have been properly prepared to receive implant components in clinically-appropriate positions.

As shown in FIG. 4, the process 400 includes step 414 where implantation of prosthetic components is facilitated. Once the bones have been prepared via step 410, the prosthetic components can be implanted. In some embodiments, step 414 is executed by the surgical system 200 by removing the robotic arm 232 from the surgical field and otherwise getting out of the way to allow a surgeon to fix the prosthetic components onto the bones without further assistance from the surgical system 200. In some embodiments, step 414 includes displaying instructions and/or navigational information that supports a surgeon in placing prosthetic components in the planned positions. In yet other embodiments, step 414 includes controlling the robotic arm 232 to place one or more prosthetic components in planned positions (e.g., holding a prosthetic component in the planned position while cement cures, while screws are inserted, constraining an impaction device to planned trajectory). Process 400 can thereby result in prosthetic components being affixed to modified bones according to an intraoperatively updated surgical plan.

Referring generally to FIGS. 5-8, features are shown which can be provided during the system setup, calibration, and registration workflow at step 404 of process 400 of FIG. 4. In particular, the features of FIGS. 5-8 relating to a portion of step 404 in which registration of the robotic arm is performed in order to allow for tracking of the robotic arm using data from the tracking system. As described in detail below, the features of FIGS. 5-8 relate to motorized movement of the robotic arm to a starting pose for a registration or calibration routine (procedure, process, workflow) for the robotic arm.

Motorized movement of the robotic arm as described below may address various challenges relating to system setup, calibration, and registration under step 404. In the example of FIG. 2, the components of the surgical system 200 are all repositionable between surgical operations. For example, the detection device 246 of the tracking system 222 may be mounted on a wheeled cart that can be moved between surgical operations. The base 230 of the robotic device 220 may also be moveable, for example provided with wheels, a steering system, and a braking system. Such mobility can facilitate use of an operating for surgeries that do not utilize the surgical system 200 in addition to operations that utilize the surgical system 200. However, such mobility can also create a challenge in properly arranging the components of the surgical system 200 for optimal functionality when the surgical system 200 is to be used in a procedure.

One aspect of this challenge is in finding a proper starting pose of the robotic arm for performing a registration or calibration routine for the robotic arm. For various reasons, for example relating to tracking accuracy, it may be desirable to perform a registration or calibration routine with a distal end of the robotic arm 232 as close as possible to where it will be during use of the robotic arm 232 during the surgical procedure. However, that location may not be readily apparent to a user, especially new users, as it should be identified at an early stage of an operation before other surgical tasks have been initiated. Additionally, a starting pose for a registration or calibration routine preferably corresponds to starting joint angles of the robotic arm 232 which will provide sufficient range of motion and degrees of freedom for the robotic arm 232 in order to complete both the registration or calibration routine and the steps of the surgical procedure. Such constraints may not be clear ahead of time to the user of a surgical system 200. Furthermore, the registration or calibration routine may require a clear line-of-sight between a trackable array coupled to a distal end of the robotic device and the detectors 246 of the tracking system throughout the registration or calibration routine, providing another constraint on selecting a proper placement of the starting pose of the robotic arm for a surgical procedure which may not be readily apparent to a user. Also, because computer-assisted navigation techniques available in later phases of a surgical operation rely upon completion of registration, such techniques are not available to assist in putting the robotic arm in a proper pose for starting a registration or calibration routine. Accordingly, a threshold challenge of providing the robotic device in a proper starting pose should be solved in order to provide a reliable, highly-accurate, user-friendly registration or calibration routine.

Figure 5:
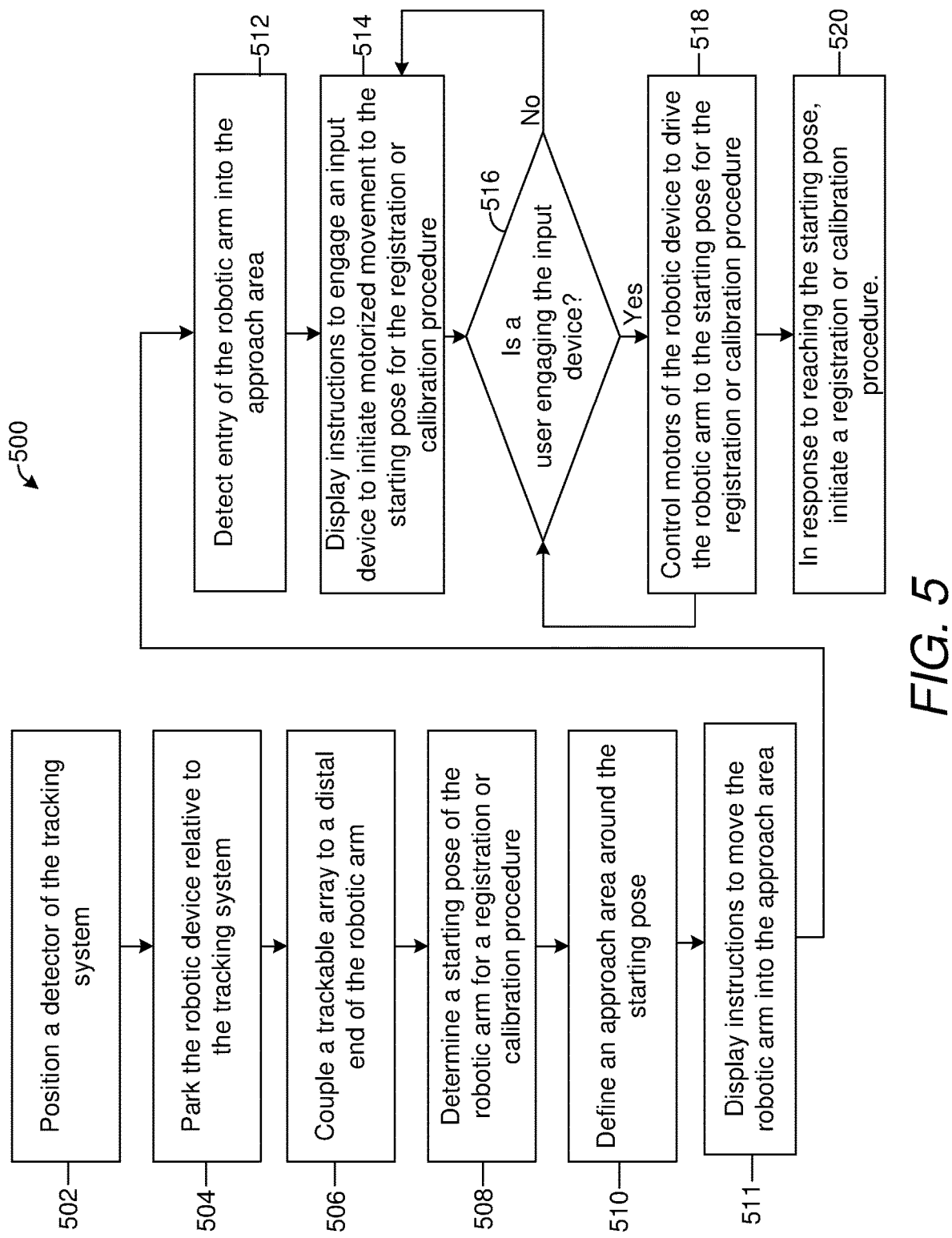
FIG. 5 is a flowchart of a process for providing a motorized movement of the robotic arm to a starting pose for a registration or calibration routine for the robotic arm, according to an exemplary embodiment.

Referring now to FIG. 5, a process 500 for providing a motorized movement of the robotic arm to a starting pose for a registration or calibration routine for the robotic arm is shown, according to an exemplary embodiment. The process 500 can be executed using the surgical system 200 described above, and reference thereto is made in the description of the process 500. The process 500 can also be used with other robotic systems in various embodiments.

At step 502, the detector 246 of the tracking system 222 is positioned, for example in an operating room. That is, the detector 246 is set (parked, locked, braked, fixed, etc.) in the position where it will preferably stay for a duration of the surgical procedure. In some embodiments, the surgical system 200 is configured to provide, via a display screen 264, instructions for positioning the detector 246 of the tracking system 222.

At step 504, the robotic device 220 and the tracking system 222 are positioned and parked relative to one another, for example such that the robotic device 220 and the detector 246 of the tracking system 222 are separated by less than or equal to a preset distance. For example, the mobile base 230 can be rolled, steered, etc. into a desired position relative to the tracking system 222 and relative to other structures in the operating room (e.g., relative to a table/bed on which a patient can be positioned during a surgical procedure). As another example, the mobile base 230 could be parked first and the tracking system 222 (e.g., the detector 246 of the tracking system 222) can be moved toward the mobile base 230. In some cases, the mobile base 230 is positioned such that the patient will be located between the mobile base 230 and the detector 246 of the tracking system 222. In some embodiments, the surgical system 200 is configured to provide, via a display screen 264, instructions for positioning the detector 246 of the tracking system 222. In some cases, the tracking system 222 is used to provide live updates of the position of the base 230 relative to a target parking position displayed on the display screen 264. Accordingly, the base 230 can be guided to a parking position relative to other components used in the operating room.

At step 506, a trackable array (fiducial tree, end effector array) is coupled to a distal end of the robotic arm 232. For example, a surgical tool 234 may be attached to the distal end of the robotic arm 232 and the trackable array can be attached to the surgical tool 234 so as to be coupled to the distal end of the robotic arm 232. As mentioned above with reference to the example of FIG. 1, a fiducial tree (tracker base array) 242 can be coupled to the base 230. In such examples, following step 506, an end effector array is positioned at a distal end of the robotic arm 232 and the base array 242 is positioned at the base 230 (e.g., proximate a proximal end of the robotic arm 232). The base array 242 is omitted in some embodiments, and may be replaced by a trackable array on the robotic arm 232 in some embodiments. In other embodiments, the trackable array is incorporated into the surgical tool 234. In yet other embodiments, machine vision is used to obtain positions of one or more of the surgical tool 234, the base 230, a point on the robotic arm 232, etc. without use of trackable arrays.

At step 508, a starting pose of the robotic arm for a registration or calibration routine is determined. The starting pose may be associated with an expected position of a surgical field in which a surgical procedure will be performed using a surgical tool 234 attached to the robotic arm 232. For example, the starting pose may be representative of cutting poses that will be used during the surgical procedure. In some embodiments, the processing circuit 260 determines the starting pose based on relative positions of the detector 246 and the base 230 of the robotic device 220. For example, the starting pose may be determined to ensure or improve the likelihood that the end effector tracker remains within the line-of-sight of the detector 246 of the tracking system 222 throughout the calibration and registration procedures. In some embodiments, the starting pose is automatically calculated based on one or more of these criteria each time the process 500 is performed (e.g., for each surgical operation). In other embodiments, the starting pose is predetermined or preprogrammed based on the various criteria, for example such that properly parking the base 230 in an acceptable position ensures that the starting pose will be properly situated in the operating room.

In some embodiments of step 508, the starting pose for registration or calibration is determined by performing an optimization process to find a best working volume for cuts in a total knee arthroplasty procedure (or other procedure in other applications). The optimization process may consider factors such as estimated calibration error for the robotic arm, anthropomorphic models of the surgeon/user relating to usability and ergonomics, surgeon height, surgeon preferences, probable position of the patient on the table, and other operating room constraints. The determination may be made using an assumption that the camera is positioned across the knee from the robotic device 220. The starting pose may be selected as the center of the optimized working volume. In some embodiments of step 508, the starting pose is selected to corresponding to a working volume where the robotic arm 232 has a lowest calibration error and estimated error due to compliance in the arm during use. Additionally, the starting pose may be selected such that motorized alignment ends in a plane that is parallel to the expected orientation of the cameras 248 of the tracking system 222.

At step 510, an approach area is defined around the starting pose. The approach area defines a space in which motorized movement of the robotic arm to the starting pose can be initiated as described below with reference to steps 512-518. In some embodiments, the approach area is defined by a virtual boundary, for example a sphere centered on the starting pose. In some embodiments, the approach area is defined in a coordinate system of the tracking system 222. In some embodiments, the approach area is defined in terms of joint angles of the robotic arm 232.

The approach area may be defined in various ways in various embodiments. For example, in some embodiments the approach area is defined to balance multiple considerations. Reducing a size of the approach area can reduce a risk of the robotic arm 232 colliding with objects or people in the operating room motorized movement. Also, determination of the approach area can include ensuring that the approach area is sufficiently large to enable a user to easily move the end effector in the approach area. The approach area can also be defined to ensure that it is consistent with the range of the robotic arm so that the robotic arm is capable of reaching the approach area. The approach area can also be sized and positioned based on a preferred distance and speed for the motorized motion in later steps, i.e., such that the robotic arm enters the approach area at a location which is within an acceptable distance of the starting pose for the registration or calibration procedure and from which the motorized motion can be performed in an acceptable amount of time (e.g., less than a threshold duration) and at an acceptable velocity (e.g., less than a threshold velocity). The approach area may vary based on whether the procedure is to be performed on a right or left side of the patient's body (e.g., right knee vs. left knee).

Figure 6:
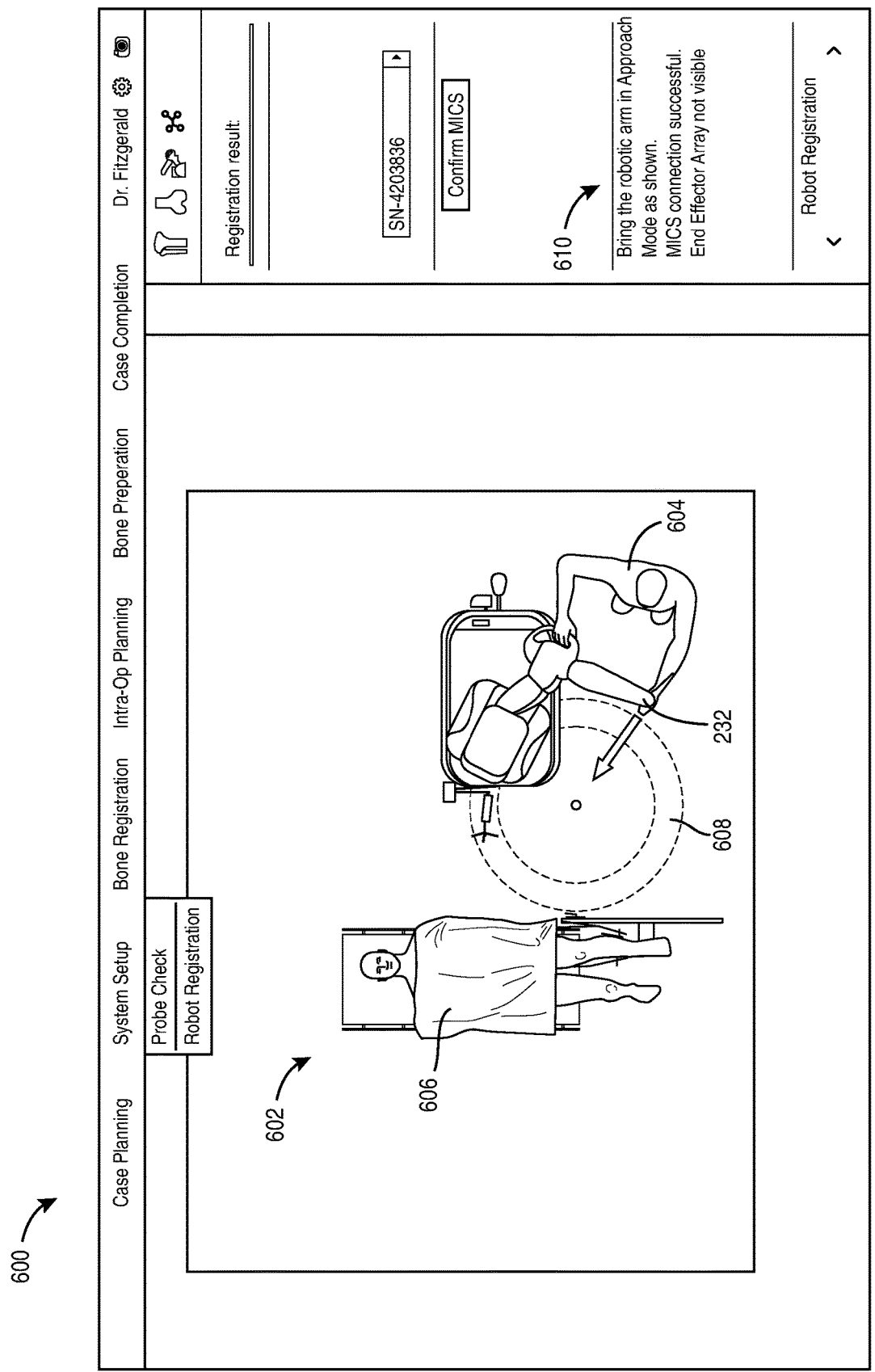
FIG. 6 is a graphical user interface that may display during execution of the process of FIG. 5, according to an exemplary embodiment.

At step 511, instructions are displayed which instruct a user to move the robotic arm into the approach area. For example, the processing circuit 260 can cause the display screen 264 to display a graphical user interface including a graphic that illustrates movement of the robotic arm into the approach area. The graphical user interface may also include text-based instructions. An example graphical user interface that can be displayed at step 511 is shown in FIG. 6 and described in detail with reference thereto below.

At step 512, entry of the robotic arm 232 into the approach area is detected. The robotic arm 232 can be moved into the approach area manually by a user. That is, the user can exert a force on the robotic arm 232 to push the robotic arm into the approach area. In some embodiments, detecting entry of the robotic arm 232 into the approach area includes tracking the end effector array (trackable markers) attached to the distal end of the robotic arm 232 with the tracking system 222 and determining whether the distal end of the robotic arm 232 is in an approach area defined in a coordinate system used by the tracking system 222. In other embodiments, detecting entry of the robotic arm 232 includes checking joint angles of the robotic arm 232 (e.g., from encoders at the joints) against one or more criteria which define the approach area in terms of joint angles of the robotic arm 232. In such embodiments, detecting entry of the robotic arm 232 into the approach area can be performed independently of the tracking system 222. Thus, step 512 corresponds to determining that the robotic arm 232 is in a position from which it can be automatically moved to the starting pose determined in step 508.

Figure 7:
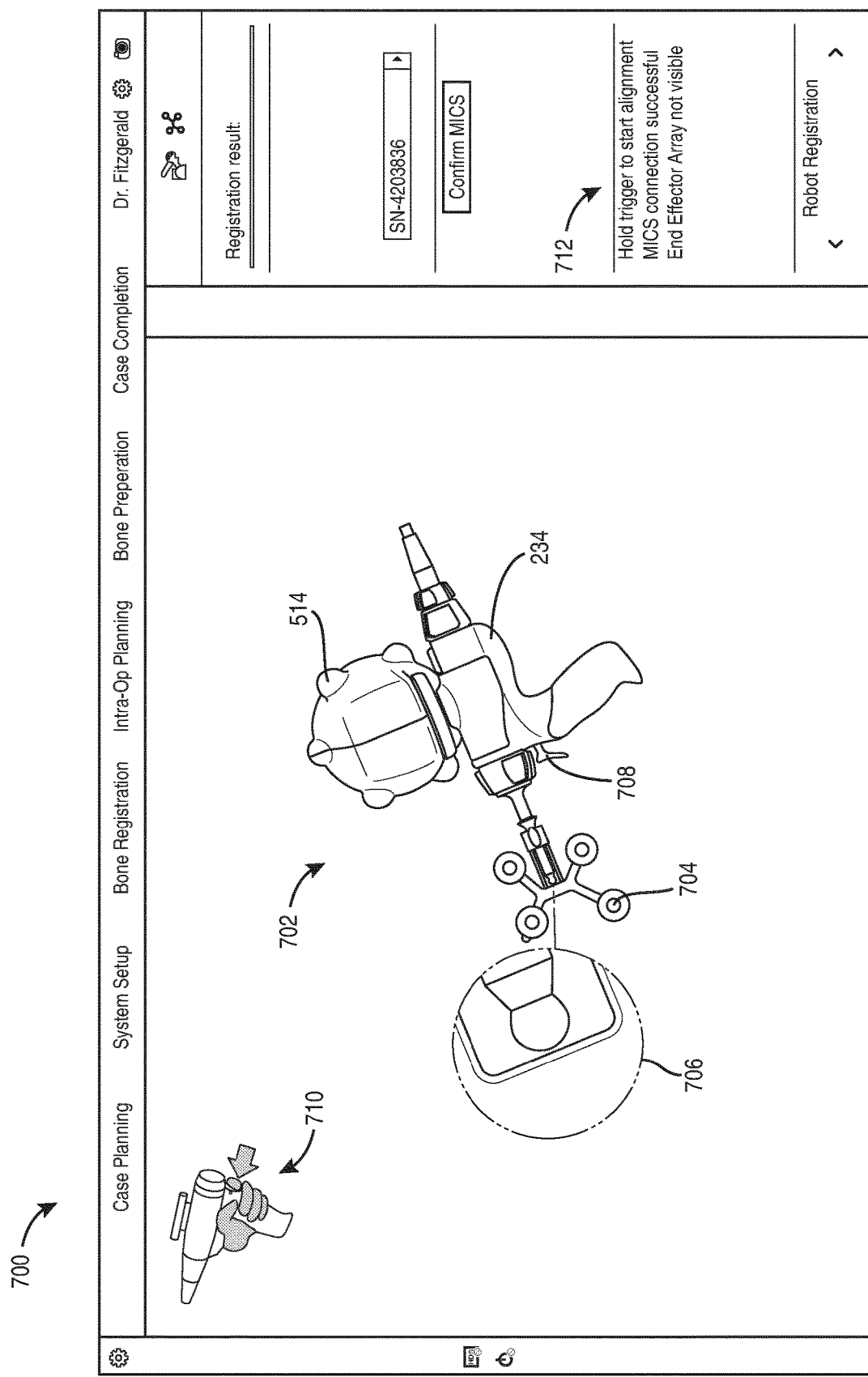
FIG. 7 is another graphical user interface that may display during execution of the process of FIG. 5, according to an exemplary embodiment.

At step 514, instructions are displayed which instruct a user to activate (e.g., engage, disengage, depress, release, etc.) an input device or otherwise input a command to initiate motorized movement of the robotic arm to the starting pose for the registration or calibration routine. For example, the processing circuit 260 may cause the display screen 264 to display a graphical user interface that includes a graphic showing a user engaging an input device, for example depressing a trigger positioned proximate the surgical tool 234, depressing a foot pedal, or otherwise engaging some other input device (e.g., mouse, button, pedal, trigger, switch, sensor). As another example, a microphone may be communicable with the processing circuit 260 such that a voice command can be used to initiate motorized movement. As another example, touchless gesture control could be used, for example using a machine vision approach, to provide a command to initiate automated alignment. As another example, the command can be input by moving the end effector in a particular direction. The command can be provided by a primary user (e.g., surgeon) in the sterile field and/or by a second person, for example a technician or nurse elsewhere in the operating room. An example user interface for display at step 514 is shown in FIG. 7 and described in detail below with reference thereto.

Accordingly, in step 514, an option is provided for the user to initiate motorized movement of the robotic arm to the starting pose for the registration or calibration routine. In alternative embodiments, steps 514 and 516 are omitted and motorized movement is automatically initiated when the robotic arm 232 enters the approach area without additional input from a user.

At step 516, a determination is made of whether the user is still activating the input device as instructed in step 514. For example, engagement of the input device (e.g., depression of a trigger) may create an electrical signal from the input device to the processing circuit 260. In such an example, the processing circuit 260 can determine whether the user is activating the input device based on whether the electrical signal is received. For example, presence of the signal from the input device may cause the processing circuit 260 to determine at step 516 that the user is engaging the input device, whereas absence of the signal from the input device may cause the processing circuit 260 to determine at step 516 that the user is not engage the input device.

If a determination is made at step 516 that the user is not activating the input device (i.e., "No" at step 516 in FIG. 5)(i.e., deactivation of the input device, for example by engagement or disengagement of an input device), the process 500 returns to step 514 to continue to display instructions to the user to engage the input device to initiate motorized movement to the starting pose. In some embodiments, an audible, haptic, or other alert may provide if the user does not engage the input device after a certain amount of time or according to some other criteria that indicates that the user is not aware of the instructions to engage the input device to initiate motorized movement to the starting pose.

If a determination is made at step 516 that the user is engaging the input device (i.e., "Yes" at step 516 in FIG. 5), the process 500 moves to step 518 where motors of the robotic arm 232 are controlled to drive the robotic arm to the starting pose for the registration or calibration routine. That is, in step 518 the robotic device 220 is controlled to provide motorized movement of the robotic arm 232 from a pose where the user first engages the input device to the starting pose for a registration or calibration routine identified in step 508. In some embodiments, motorized movement is performed along a shortest/straight path to the starting pose. In some embodiments, step 518 includes automatically planning a path between an initial position and the starting poses for the registration or calibration routine, and then control the robotic arm to provide movement along the planned path. The path can be straight or curved. In some embodiments, the path is planned such that motorized movement of the robotic arm 232 in step 518 will take between a lower duration threshold and an upper duration threshold (e.g., between approximately 4 seconds and approximately six seconds).

Motorized movement of the robotic arm 232 to the starting pose in step 518 can includes movement in one to six degrees of freedom, for example including moving a distal end of the robotic arm 232 to a location identified by the starting pose and providing rotations to align with an orientation identified by the starting pose. In some embodiments, motorized movement includes arranging joint angles of the robotic arm 232 in a preferred (e.g., predefined) arrangement, for example an arrangement that facilitate calibration, registration, and/or completion of the surgical procedure. In other embodiments, for example for a seven degree of freedom robot, motorized movement can be performed such that the target starting position of the end effector (surgical tool 234) is defined and used for control without regards to angles or other positions of the arm 232.

As illustrated in FIG. 5, the processing circuit 260 can continue to make the determination in step 516 of whether the user is engaging the input device. In some scenarios, the user will engage the input device to initiate motorized movement, but then disengage from the input device before the motorized movement has resulted in arrival at the starting pose for the registration or calibration routine. In such scenarios, and in some embodiments, the processing circuit 260 determines in step 516 that the user is no longer engaging the input device and stops the motorized movement of the robotic arm. Process 500 can then return to step 514, where a user is instructed to restart motorized movement by reengaging the input device.

If the user continues to engage the input device, motorized movement continues until the robotic arm 232 reaches the starting pose for the registration or calibration routine. At step 520, in response to reaching the starting pose, a registration or calibration routine is initiated. Initiating the registration or calibration routine can include starting one or more data collection processes, for example tracking of an end effector array and base array by the tracking system 222, any other tracking of the robotic device 220, controlling the robotic arm 232 to provide additional motorized movements or to constrain manual movement of the robotic arm 232, and/or providing instructions for user actions to support the registration or calibration routine via the display screen 264.

For example, FIG. 8 (described in detail below) shows a graphical user interface that can be displayed via the display screen 264 in response to the robotic arm 232 reaching the starting pose for the registration or calibration routine. As described in detail below, the registration or calibration routine in the example of FIG. 8 includes providing instructions to a user to cause the user to manually move the distal tip of the surgical tool 234 coupled to the robotic arm 232 to the vertices of a cube while the end effector array is in view of the detector 246 of the tracking system. The cube in such an example is located proximate the starting pose for the registration or calibration routine identified in step 508, for example centered on the starting point or having a first vertex at the starting pose. The motorized movement to the starting pose can be seen as guiding the surgical tool 234 and/or tracking array to this cube. Geometries other than a cube can be used in other embodiments, for example selected such that each joint of the arm is exercised during the registration or calibration routine.

By ensuring that the registration or calibration routine (procedure) is performed from the system-determined starting pose, process 500 can reduce or eliminate potential human-caused variations in initiation of the registration or calibration routine, which may increase the reliability and accuracy of the registration or calibration routine. Additionally, by providing motorized movement to the starting pose, efficiency and usability of the system can be improved. The process 500 thereby provides improvements over alternative approaches to initiating a registration or calibration routine.

Referring now to FIG. 6, a graphical user interface 600 is shown, according to an exemplary embodiment. The graphical user interface 600 can be displayed on the display screen 264 under control of the processing circuit 260. The graphical user interface 600 displays instructions for moving the robotic arm 232 into an approach area for initiation of motorized movement, and can correspond to step 511 of process 500. The graphical user interface shows a graphic 602 illustrating a user 604 manually pushing a distal end of the robotic arm 232 into an approach area 606, including an illustration of a preferred grip or handling technique for manipulating the robotic arm 232 to move the robotic arm 232 into approach area 606. The graphic 602 includes a depiction of the patient 608 to facilitate a user in determining which direction to move the robotic arm (e.g., toward the patient as illustrated in FIG. 6). In some embodiments, the graphic 602 is updated in real-time (i.e., at a high enough frequency to appear as real-time to a typical user) to depict actual, real-time movement of the robotic arm 232. The graphic 602 is designed to be intuitive for a user to interpret and follow in order to move the robotic arm 232 into the approach area in accordance with step 511 of process 500.

The graphical user interface 600 also includes text-based messages 610 that can include instructions, alerts, warning, updates, etc. with respect to operation of the surgical system 200. In the example shown, the text-based messages 610 include instructions to bring the robotic arm 232 in Approach Mode as shown, i.e., to move the robotic arm 232 into the approach area as illustrated in the graphic 602. The text-based messages 610 also indicate that the surgical tool is successfully connected to the robotic arm, and that the end effector array is not currently visible to the detector 246 of the tracking system. Motorized movement via process 500 can move the end effector from outside the field of view of the detector 246 as indicated by the text-based messages 610 and into the field of view of the detector 246 to enable a registration or calibration routine. Information can also be communicated to the user via sounds emitted by a speaker of the surgical system 200 (e.g., acoustic feedback), forces provided via the robotic device 220 (e.g., haptic feedback), or indicators lights positioned on the robotic arm 232 or elsewhere in the surgical system 200. These various types of feedback can be provided at various events in operation of the surgical system 200, for example when the approach area is entered, when motorized movement can be initiated, when motorized movement is initiated, successful motorized movement, and/or successful or unsuccessful completion of various other events and steps described herein.

A user can follow the graphical and text-based instructions of graphical user interface 600 (and/or acoustic or haptic feedback) to move the robotic arm 232 into the approach area 606. In response, the processing circuit 260 detects entry of the robotic arm 232 into the approach area at step 512, and updates the display screen 264 to display instructions to engage an input device to initiate motorized movement to the starting pose for the registration or calibration routine at step 514 as in FIG. 7, for example.

Referring now to FIG. 7, a graphical user interface 700 that can be displayed on the display screen 264 at step 514 is shown, according to an exemplary embodiment. The graphical user interface 700 is configured to instruct a user to engage an input device or otherwise input a command to initiate motorized movement of the robotic arm to the starting pose. The graphical user interface 700 is also configured to instruct a user to check whether an end effector array is properly mounted on the surgical tool 234. For example, the graphical user interface 700 may display a quality metric based on the orientation of the end effector and a result of checking whether the end effector array is fully seated. The graphical user interface 700 may display a warning or instructions to correct the mounting on the end effector array in some scenarios, for example if an improper orientation of the end effector array is detected.

The graphical user interface 700 includes a graphic 702 of the surgical tool 234 attached to the distal end of the robotic arm 232, as is the case when step 514 of process 500 is initiated. The graphic 702 shows an end effector array 704 attached to the surgical tool, and includes a call-out window 706 showing a zoomed-in view of an interface between the end effector array 704 and the surgical tool 234. The graphic 702 shows the end effector array 704 as properly attached to the surgical tool 234, such that the graphic 702 may thereby encourage a user to verify that this connection is properly made at the physical surgical tool. The graphic 702 also shows that the surgical tool 234 includes a trigger 708. In other embodiments, another input device is shown instead of the trigger 708 (e.g., foot pedal, mouse, button, switch, sensor).

The graphical user interface 700 also includes an icon 710 configured to communicate an instruction to press the trigger 708. The icon 710 includes a depiction of the surgical tool 234, including the trigger 708 and a hand holding a grip portion of the surgical tool 234 with a finger of the hand positioned on the trigger 708. An arrow is included in the icon 710 indicating that the finger is depressing the trigger 708. The icon 710 is thereby configured to show depression of the trigger 708 by a user. In embodiments where other types of commands are received to initiate the motorized movement, the icon 710 can be adapted accordingly. For example, the icon 710 can show depression or release of a foot pedal, selection of a button, engagement of some other sensor, verbal statement of a command (e.g., "Okay Robot, Start Movement"), user gesture or body movement, etc. as appropriate in various embodiments to indicate to the user that the system is ready to accept the user input to initiate the motorized movement.

The graphical user interface 700 also includes text-based messages 712 that can include instructions, alerts, updates, statuses, warnings, etc. regarding operation of the surgical system 200. As shown in FIG. 7, the text-based messages 712 includes instructs to hold the trigger 708 to start alignment, i.e., to initiated motorized movement to the starting pose for the registration or calibration routine. The text-based messages 712 also indicate that the also indicate that the surgical tool is successfully connected to the robotic arm, and that the end effector array is not currently visible to the detector 246 of the tracking system, or provide other information relating to occlusion of one or more tracking arrays. Motorized movement via process 500 can move the end effector from outside the field of view of the detector 246 as indicated by the text-based messages 610 and into the field of view of the detector 246 to enable a registration or calibration routine. In contrast to other alignment, navigation, or control functionality in other portions of a procedure where control is performed based on data from the tracking system 222, the motorized movement here can be initiated without visibility of the end effector or the end effector array to the detector 246, without visibility of the base array to the detector 246, and before calibration and registration have been performed.

When the trigger 708 (or other input device in various embodiments) is engaged or activated, for example by depression of the trigger 708 as instructed in the graphical user interface 700 as shown in FIG. 7, the robotic device 220 can be controlled to cause motorized movement of the robotic arm 232 to the starting pose for the registration or calibration routine (i.e., steps 516-518 of process 500). The graphical user interface 700 can continue to be displayed during motorized alignment, for example updated with an icon or text-based message 712 indicating that motorized movement is occurring and that the trigger 708 (or other input device in various embodiments) can be deactivated or disengaged (e.g., released, un-depressed) to pause the motorized movement. The input device may work as a dead-man switch so that the motorized movement is stopped if the input device is released, but may also work as a selectable brake in some embodiments, i.e., such that an input device can be engaged to pause the motorized movement. In response to reaching the starting pose (i.e., step 520), the processing circuit 260 can cause the display screen to display the graphical user interface 800 shown in FIG. 8.

Figure 8:
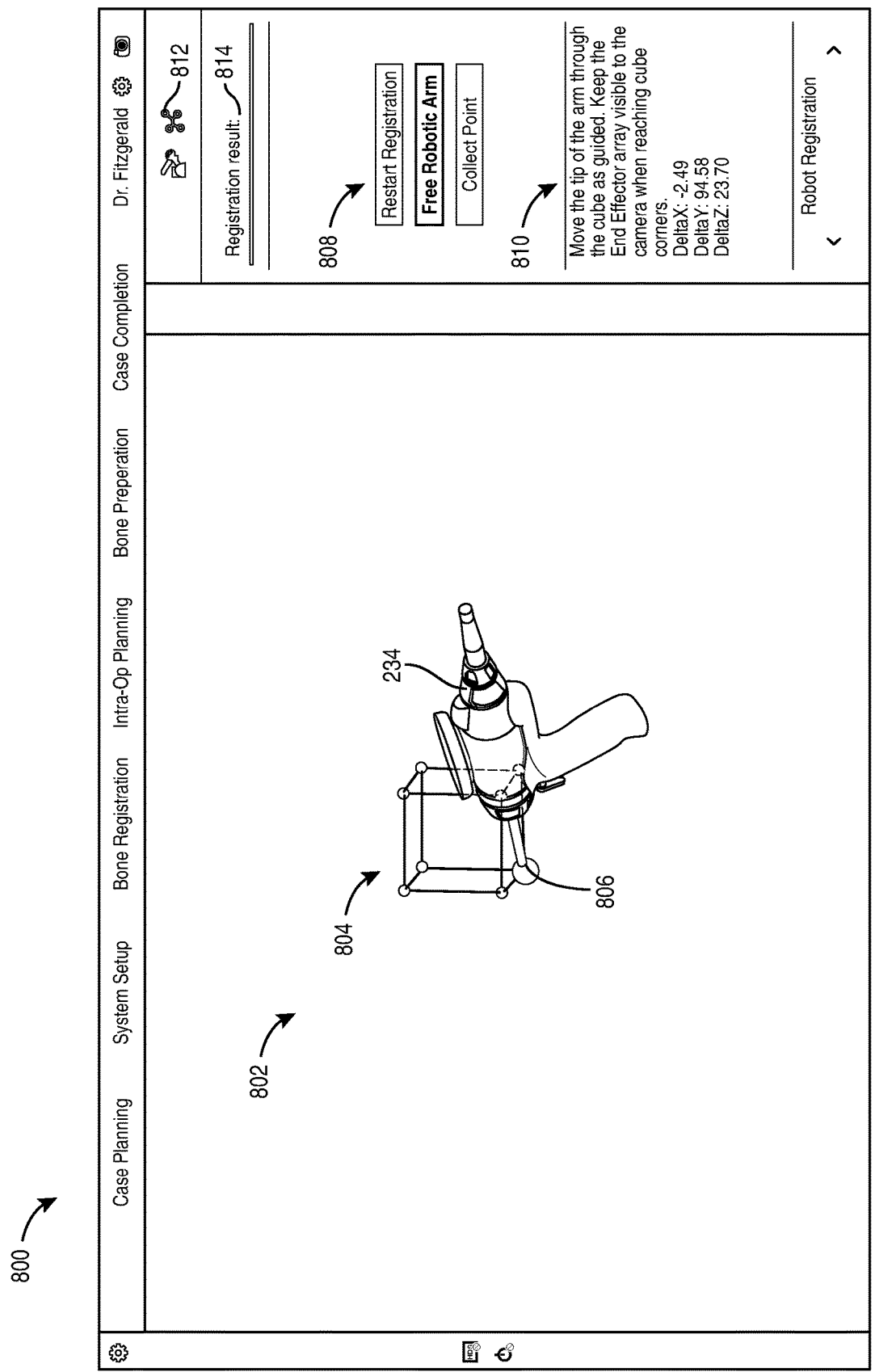
FIG. 8 is yet another graphical user interface that may display during execution of the process of FIG. 5, according to an exemplary embodiment.

Referring now to FIG. 8, a graphical user interface 800 guiding a user through a registration or calibration routine for the robotic arm 232 is shown, according to an exemplary embodiment. In the embodiment shown, the graphical user interface 800 includes a graphic 802 instructing the user to manually move the surgical tool 234 through a series of positions. In particular, the graphic 802 guides a user in moving a tracked tip 806 of the surgical tool 234 to vertices of a virtual cube 804. The virtual cube 804 corresponds to a volume in real space proximate the starting pose for the registration or calibration routine, with vertices positioned several inches from one another, for example. Other geometries can be used in various embodiments, for example selected to ensure that all joints are exercised during the registration or calibration routine. The virtual cube 804 includes vertices that can change colors to indicate the next vertex the tip 806 of the surgical tool 234 should be moved to, which vertices have already been contacted by the tip 806 of the surgical tool 234, and which vertices have not yet been contacted by the tip 806 of the surgical tool 234. The graphical user interface 800 can be updated in real-time such that movement of the real, physical surgical tool 234 causes corresponding movement of the virtual representation of the surgical tool 234 in the graphical user interface 800. The graphic 802 thereby provides real-time navigational guidance to facilitate the user in performing manual movements of the surgical tool 234 to complete a registration or calibration routine. In other embodiments, automated movements are used.

The graphical user interface 800 is also shown as including selectable buttons 808 that allow a user to select to restart the registration or calibration routine, free the robotic arm from the registration or calibration routine, or collect a point (i.e., record a position of end effector tracker as part of the registration or calibration routine). The graphical user interface 800 thereby provides interactivity with and control over the registration or calibration routine. The graphical user interface 800 also shows text-based instructions 810 explaining how the robotic arm is to be moved through the virtual cube 804 as guided in the graphic 802 while keeping the end effector array visible to the detector 246 of the tracking system 222. A sound can be emitted from the surgical system 200 at each successful capture (e.g., when the end effector meets a vertex of the virtual cube 804). A haptic feedback, for example a vibration, or an indicator light can also be used to indicate a successful capture during the registration or calibration process.

The text-based instructions 810 may include real-time coordinates of the tracked tip of the surgical tool 234 which may be useful to a user. The graphical user interface 800 is also shown as including an icon 812 which can change colors to indicate whether the end effector array is currently visible to the detector 246 (e.g., red for not visible, green for visible). Other icons may be similarly included to show connectivity, proper operation, etc. of other components of the surgical system 200. The graphical user interface 800 is also shown to include a registration results progress bar 814 which can update to show progress through the registration process and/or indicate a quality of the registration process.

The graphical user interface 800 thereby includes various features which may be helpful in guiding a user through a registration or calibration routine for the surgical system 200 starting at and following step 520 of process 500. In some embodiments, for example the example shown in FIGS. 7-8, successful completion of the registration or calibration routine allows the end effector array 704 to be removed from the surgical tool 234 while enabling the tracking system 222 to accurately determine positions of the surgical tool 234 by tracking the base array 242 and using data indicating rotations of joints of the robotic arm 232. In such examples, various steps of processes 300 and 400 can then be performed without a trackable marker attached directly to the surgical tool 234. It should be noted that the automated, motorized movement of process 500 occurs before registration or calibration is completed to enable the tracking and control approaches used for the robotic arm 232 in later steps of process 400, for example during bone preparation.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, magnetic, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

What is claimed is:

1. A surgical system comprising:
   a robotic arm extending from a base;
   a tracking system configured to track at least one of a first marker attached to a distal end of the robotic arm and a second marker attached to the base;
   a controller configured to:
      in response to the robotic arm entering an approach area, provide an option to initiate automatic movement to a starting pose for a registration or calibration routine for the robotic arm;
      in response to selection of the option, control the robotic arm to automatically move to the starting pose for the registration or calibration routine; and
      in response to successful automatic movement to the starting pose for the registration or calibration routine, perform the registration or calibration routine for the robotic arm.

2. The surgical system of claim 1, wherein the robotic arm is configured to be manually moved into the approach area, and wherein the starting pose for the registration or calibration routine is spaced apart from a patient.

3. The surgical system of claim 1, further comprising a display screen and an input device, wherein the controller is configured:
   cause the display screen to display a first graphic instructing a user to move the robotic arm into the approach area;
   in response to the robotic arm entering the approach area, cause the display screen to display a second graphic instructing the user to engage the input device to select the option to initiate the automatic movement.

4. The surgical system of claim 1, wherein the controller is configured to control the robotic arm to automatically move to the starting pose for the registration or calibration routine by:
   providing the automatic movement if an input device of the robotic device is activated; and
   stopping the automatic movement if the input device is not activated.

5. The surgical system of claim 4, wherein the input device is a trigger positioned at a distal end of the robotic arm.

6. The surgical system of claim 1, comprising the first marker attached to the distal end of the robotic arm and the second marker attached to the base;
   wherein the registration or calibration routine provides registration of the distal end of the robotic arm relative to the marker attached to the base based on data from the tracking system indicating tracked positions of the marker attached to the distal end of the robotic device.

7. The surgical system of claim 1, wherein the controller is configured to determine, prior to the automatic movement of the robotic arm to the starting pose for the registration or calibration routine, the starting pose for the registration or calibration routine based on an expected position of a surgical field relative to the base.

8. A method of controlling a robotic arm mounted on a movable base, comprising:
   in response to the robotic arm entering an approach area, providing an option to initiated automatic movement to a starting pose for a registration or calibration routine for the robotic arm;
   in response to selection of the option, controlling the robotic arm to automatically move to the starting pose for the registration or calibration routine; and
   in response to successful automatic movement to the starting pose for the registration or calibration routine, providing the registration or calibration routine for the robotic arm.

9. The method of claim 8, further comprising allowing the robotic arm to be manually moved into the approach area, wherein the approach area and the starting pose for the registration or calibration routine are spaced apart from a patient.

10. The method of claim 9, further comprising:
displaying, via display screen, a first graphic instructing a user to move the robotic arm into the approach area; and
in response to the robotic arm entering the approach area, displaying, via the display screen to display a second graphic instructing the user to activate an input device to initiate the automatic movement.

11. The method of claim 10, wherein controlling the robotic arm to automatically move to the starting pose for the registration or calibration routine in response to selection of the option comprises:
providing the automatic movement if the input device of the robotic device is activated; and
stopping the automatic movement if the input device is not activated.

12. The method of claim 8, wherein providing the registration or calibration routine comprises tracking, with the tracking system, a first marker attached to the distal end of the robotic arm relative to a second marker attached to the base while the distal end of the robotic arm completes movements of the registration or calibration routine, wherein the movements of the registration or calibration routine comprise automated movements or manual movements.

13. The method of claim 8, wherein the registration or calibration routine is configured to register the distal end of the robotic arm relative to a base tracking array attached to the base such that a position of the distal end of the robotic arm can be defined based on a tracked position of the base tracking array collected by the tracking system and angles of joints of the robotic arm.

14. The method of claim 8, wherein determining the starting pose comprises calculating, prior to the automatic movement of the robotic arm to the starting pose for the registration or calibration routine, the starting pose based on a position of the movable base.

15. One or more non-transitory computer-readable media storing program instructions that, when executed by one or more processors, cause the one or more processors to perform operations comprising:
in response to a robotic arm entering an approach area, providing an option to initiate automatic movement to a starting pose for a registration or calibration routine for a robotic arm;
in response to selection of the option, controlling the robotic arm to automatically move the robotic arm to the starting pose; and
in response to successful automatic movement to the starting pose for the registration or calibration routine, providing the registration or calibration routine for the robotic arm.

16. The non-transitory computer-readable media of claim 15, wherein the starting pose for the registration or calibration routine is spaced apart from a patient.

17. The non-transitory computer-readable media of claim 16, the operations further comprising:
causing a display screen to display a first graphic instructing a user to move the robotic arm into the approach area; and
in response to the robotic arm entering the approach area, causing the display screen to display a second graphic instructing the user to engage an input device to initiate the automatic movement.

18. The non-transitory computer-readable media of claim 15, wherein controlling the robotic arm to automatically move to the starting pose for the registration or calibration routine comprises:
receiving a signal indicative of whether an input device of the robotic device is being engaged by a user;
providing the automatic movement if an input device of the robotic device is being engaged by the user; and
stopping the automatic movement if the input device is not being engaged by the user.

19. The non-transitory computer-readable media of claim 15, wherein providing the registration or calibration routine comprises obtaining tracked positions of a first marker attached to the distal end of the robotic arm relative to a second marker attached to the base while the distal end of the robotic arm completes movements of the registration or calibration routine.

20. The non-transitory computer-readable media of claim 15, wherein determining the starting pose comprises calculating, prior to the automatic movement, the starting pose based on the position of the base.

* * * * *